United States Patent
Parkhurst et al.

(10) Patent No.: US 9,487,573 B2
(45) Date of Patent: Nov. 8, 2016

(54) MURINE ANTI-NY-ESO-1 T CELL RECEPTORS

(71) Applicant: The United States of America, as represented by the Secretary, Department of Health and Human Services, Washington, DC (US)

(72) Inventors: Maria R. Parkhurst, Ellicott City, MD (US); Richard A. Morgan, Columbia, MD (US); Steven A. Rosenberg, Potomac, MD (US); Shannon Faith Rosati, Richmond, VA (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/401,893

(22) PCT Filed: May 22, 2013

(86) PCT No.: PCT/US2013/042162
§ 371 (c)(1),
(2) Date: Nov. 18, 2014

(87) PCT Pub. No.: WO2013/177247
PCT Pub. Date: Nov. 28, 2013

(65) Prior Publication Data
US 2015/0141347 A1 May 21, 2015

Related U.S. Application Data

(60) Provisional application No. 61/650,020, filed on May 22, 2012.

(51) Int. Cl.
| | |
|---|---|
| *C07K 14/725* | (2006.01) |
| *C07K 7/06* | (2006.01) |
| *C07K 7/08* | (2006.01) |
| *C07K 16/18* | (2006.01) |
| *C07K 16/28* | (2006.01) |
| *G01N 33/574* | (2006.01) |
| *A61K 38/00* | (2006.01) |

(52) U.S. Cl.
CPC ............ *C07K 14/7051* (2013.01); *C07K 7/06* (2013.01); *C07K 7/08* (2013.01); *C07K 16/18* (2013.01); *C07K 16/2809* (2013.01); *G01N 33/57492* (2013.01); *A61K 38/00* (2013.01); *C07K 2317/20* (2013.01); *C07K 2317/21* (2013.01); *C07K 2319/00* (2013.01); *G01N 2333/7051* (2013.01)

(58) Field of Classification Search
None
See application file for complete search history.

(56) References Cited

U.S. PATENT DOCUMENTS

| | | |
|---|---|---|
| 4,450,150 A | 5/1984 | Sidman |
| 5,087,616 A | 2/1992 | Myers et al. |
| 5,225,539 A | 7/1993 | Winter |
| 5,449,752 A | 9/1995 | Fujii et al. |
| 5,545,806 A | 8/1996 | Lonberg et al. |
| 5,569,825 A | 10/1996 | Lonberg et al. |
| 5,585,089 A | 12/1996 | Queen et al. |
| 5,639,641 A | 6/1997 | Pedersen et al. |
| 5,693,761 A | 12/1997 | Queen et al. |
| 5,714,352 A | 2/1998 | Jakobovits |
| 7,329,731 B2 | 2/2008 | Jakobsen et al. |
| 7,915,036 B2 | 3/2011 | Morgan et al. |
| 8,008,438 B2 | 8/2011 | Boulter et al. |
| 8,088,379 B2 | 1/2012 | Robbins et al. |
| 2003/0220239 A1 | 11/2003 | Simard et al. |
| 2009/0304657 A1 | 12/2009 | Morgan et al. |
| 2010/0297093 A1 | 11/2010 | Robbins et al. |

FOREIGN PATENT DOCUMENTS

| | | |
|---|---|---|
| EP | 0 239 400 B1 | 8/1994 |
| GB | 2 188 638 A | 10/1987 |
| WO | WO 2009/042570 A2 | 4/2009 |
| WO | 2012/038055 A1 | 3/2012 |

OTHER PUBLICATIONS

Cohen et al. ("Enhanced Antitumor Activity of Murine-Human Hybrid T-cell Receptor (TCR) in Human Lymphocytes is Associated with Improved Pairing and TCR/CD3 Stability" Cancer Research 2006; 66 (17)).*
Anderton et al., "Selection and fine-tuning of the autoimmune T-cell repertoire," *Nat. Rev. Immunol.*, 2 (7), 487-498 (2002).
Bialer et al., "Selected murine residues endow human TCR with enhanced tumor recognition," *J. Immunol.*, 184 (11), 6232-6241 (2010).
Caballero et al., "Cancer/testis (CT) antigens: potential targets for immunotherapy," *Cancer Sci.*, 100 (11), 2014-2021 (2009).
Casado et al., "Lentivector immunization induces tumor antigen-specific B and T cell responses in vivo," *Eur. J. Immunol.*, 38 (7), 1867-1876 (2008).
Choi et al., "Synthesis and assembly of a cholera toxin B subunit-rotavirus VP7 fusion protein in transgenic potato," *Mol. Biothechnol.*, 31 (3), 193-202 (2005).
Cohen et al., "Enhanced antitumor activity of murine

(56) References Cited

OTHER PUBLICATIONS

Goff et la., "Enhanced receptor expression and in vitro effector function of a murine-human hybrid MART-1-reactive T cell receptor following a rapid expansion," *Cancer Immunol. Immunother.*, 59 (10), 1551-1560 (2010).

Haskard et al., "The production of human monoclonal autoantibodies from patients with rheumatoid arthritis by the EBV-hybridoma technique," *J. Immunol. Methods*, 74 (2), 361-367 (1984).

Hudecz, "Synthesis of peptide bioconjugates," *Methods Mol. Biol.*, 298, 209-223 (2005).

Huse et al., "Generation of a large combinatorial library of the immunoglobulin repertoire in phage lambda," *Science*, 246 (4935), 1275-1281 (1989).

International Preliminary Report on Patentability, Application No. PCT/US2013/042162, dated Nov. 25, 2014.

International Search Report, Application No. PCT/US2013/042162, dated Aug. 9, 2013.

Johannsen et al., "Definition of key variables for the induction of optimal NY-ESO-1-specific T cells in HLA transgene mice," *J.Immunol.*, 185 (6), 3445-3455 (2010).

Kirin et al., "Amino acid and peptide bioconjugates of copper(II) and zinc(II) complexes with a modified N,N-bis(2-picolyl)amine ligand," *Inorg. Chem.*, 44 (15), 5405-5415 (2005).

Köhler et al., "Derivation of specific antibody-producing tissue culture and tumor lines by cell fusion," *Eur. J. Immunol.*, 6 (7), 511-519 (1976).

Kuball et al., "Cooperation of Human Tumor-Reactive CD4+ and CD8+ T Cells after Redirection of Their Specificity by a High-Affinity p53A2.1-Specific TCR," *Immunity*, 22 (1), 117-129 (2005).

Lee et al., "NY-ESO-1 may be a potential target for lung cancer immunotherapy," *Cancer J. Sci. Am.*, 5 (1), 20-25 (1999).

Leisegang et al., "Enhanced functionality of T cell receptor-redirected T cells is defined by the transgene cassette," *J. Mol. Med.*, 86 (5), 573-583 (2008).

Naviaux et al., "The pCL vector system: rapid production of helper-free, high-titer, recombinant retroviruses," *J. Virol.*, 70 (8), 5701-5705 (1996).

Palmer, "Negative selection—clearing out the bad apples from the T-cell repertoire," *Nat. Rev. Immunol.*, 3 (5), 383-391 (2003).

Parkhurst et al., "Characterization of genetically modified T-cell receptors that recognize the CEA:691-699 peptide in the context of HLA-A2.1 on human colorectal cancer cells," *Clin. Cancer Res.*, 15 (1), 169-180 (2009).

Pedersen et al., "Comparison of surface accessible residues in human and murine immunoglobulin Fv domains. Implication for humanization of murine antibodies," *J. Mol. Biol.*, 235 (3), 959-973 (1994).

Rao et al., "Inhibition of histone lysine methylation enhances cancer-testis antigen expression in lung cancer cells: implications for adoptive immunotherapy of cancer," *Cancer Res.*, 71 (12), 4192-4204 (2011).

Reiter et al., "Engineering interchain disulfide bonds into conserved framework regions of Fv fragments: improved biochemical characteristics of recombinant immunotoxins containing disulfide-stabilized Fv," *Protein Eng.*, 7 (5), 697-704 (1994).

Riddell et al., "Restoration of viral immunity in immunodeficient humans by the adoptive transfer of T cell clones," *Science*, 257 (5067), 238-241 (1992).

Robbins et al., "Single and dual amino acid substitutions in TCR CDRs can enhance antigen-specific T cell functions," *J. Immunol.*, 180 (9), 6116-6134 (2008).

Robbins et al., "Tumor regression in patients with metastatic synovial cell sarcoma and melanoma using genetically engineered lymphocytes reactive with NY-ESO-1," *J. Clin. Oncol.*, 29 (7), 917-924 (2011).

Roder et al., "The EBV-hybridoma technique," *Methods Enzymol.*, 121, 140-167 (1986).

Schmid et al., "Evidence for a TCR Affinity Threshold Delimiting Maximal CD8 T Cell Function," *J. Immunol.*, 184 (9), 4936-4946 (2010).

Wadhwa et al., "Receptor mediated glycotargeting," *J. Drug Target.*, 3 (2), 111-127 (1995).

Wargo et al., "Recognition of NY-ESO-1+ tumor cells by engineered lymphocytes is enhanced by improved vector design and epigenetic modulation of tumor antigen expression," *Cancer Immunol. Immunother.*, 58 (3), 383-394 (2009).

Written Opinion of the International Searching Authority, Application No. PCT/US2013/042162, dated Aug. 9, 2013.

* cited by examiner

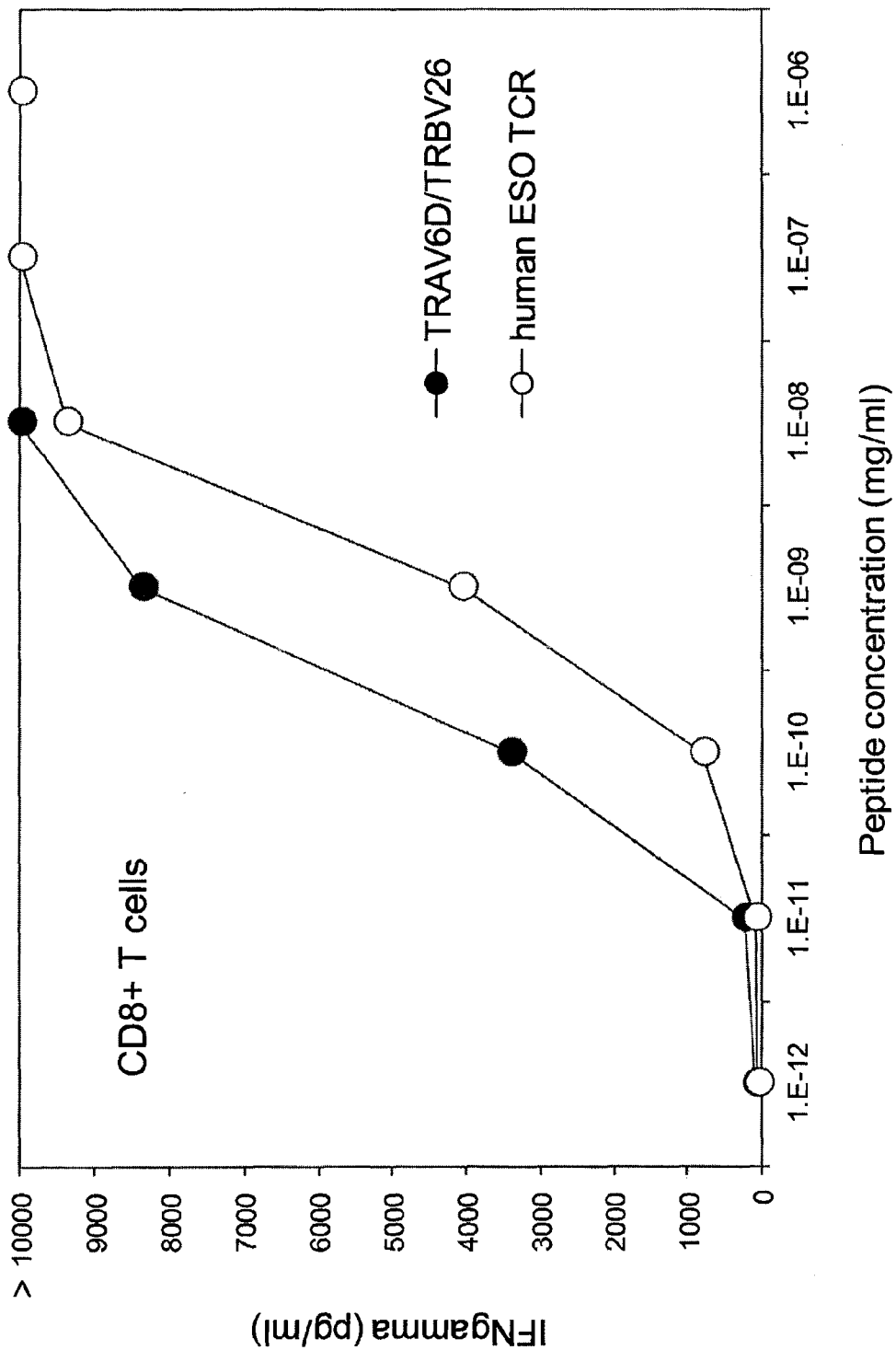

MURINE ANTI-NY-ESO-1 T CELL RECEPTORS

CROSS REFERENCE TO RELATED APPLICATION

This patent application is the U.S. National Phase of International Patent Application No. PCT/US2013/042162, filed May 22, 2013, which claims the benefit of U.S. Provisional Patent Application No. 61/650,020, filed May 22, 2012, each of which is incorporated by reference in its entirety herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: one 23,509 Byte ASCII (Text) file named "719030ST25.TXT," dated Nov. 3, 2014.

BACKGROUND OF THE INVENTION

Adoptive cell therapy can be an effective treatment for cancer in some patients. However, obstacles to the overall success of adoptive cell therapy still exist. For example, only 50% of melanoma tumor samples may generate tumor reactive T-cells. Generating tumor-reactive T-cells from non-melanoma cancers can also be difficult. Moreover, many patients may not have a tumor that is amenable to surgical resection. Accordingly, there is a need for T-cell receptors for use in treating patients with cancer.

BRIEF SUMMARY OF THE INVENTION

The invention provides an isolated or purified T-cell receptor (TCR) having antigenic specificity for NY-ESO-1 and comprising a murine variable region. The invention also provides related polypeptides and proteins, as well as related nucleic acids, recombinant expression vectors, host cells, and populations of cells. Further provided by the invention are antibodies, or an antigen binding portion thereof, and pharmaceutical compositions relating to the TCRs of the invention.

Methods of detecting the presence of cancer in a mammal and methods of treating or preventing cancer in a mammal are further provided by the invention. The inventive method of detecting the presence of cancer in a mammal comprises (i) contacting a sample comprising cells of the cancer with any of the inventive TCRs, polypeptides, proteins, nucleic acids, recombinant expression vectors, host cells, populations of host cells, or antibodies, or antigen binding portions thereof, described herein, thereby forming a complex, and (ii) detecting the complex, wherein detection of the complex is indicative of the presence of cancer in the mammal.

The inventive method of treating or preventing cancer in a mammal comprises administering to the mammal any of the TCRs, polypeptides, or proteins described herein, any nucleic acid or recombinant expression vector comprising a nucleotide sequence encoding any of the TCRs, polypeptides, proteins described herein, or any host cell or population of host cells comprising a recombinant vector which encodes any of the TCRs, polypeptides, or proteins described herein, in an amount effective to treat or prevent cancer in the mammal.

BRIEF DESCRIPTION OF THE SEVERAL VIEWS OF THE DRAWING(S)

FIGS. 1A and 1B are graphs showing interferon (IFN)-γ secretion by human CD8+ (FIG. 1A) or CD4+ (FIG. 1B) T cells transfected with a murine anti-NY-ESO-1 TCR (shaded circles) or a human anti-NY-ESO-1 TCR (unshaded circles) upon co-culture with dendritic cells pulsed with various concentrations of NY-ESO-$1_{157-165}$.

FIGS. 2A and 2B are graphs showing IFN-γ secretion by human CD8+ (FIG. 2A) or CD4+ (FIG. 2B) T cells transfected with a murine anti-NY-ESO-1 TCR (shaded bars) or a human anti-NY-ESO-1 TCR (unshaded bars) cultured alone (media) or co-cultured with T2 cells pulsed with control peptide, T2 cells pulsed with NY-ESO-$1_{157-165}$ peptide, or one of various tumor cell lines 888mel (NY-ESO-1⁻), Sk23mel (NY-ESO-1⁻), COA-A2-CEA (NY-ESO-1⁻), A375mel (NY-ESO-1⁺), 1363mel (NY-ESO-1⁺), or COS-A2-ESO (NY-ESO-1⁺).

DETAILED DESCRIPTION OF THE INVENTION

Figure 1B:
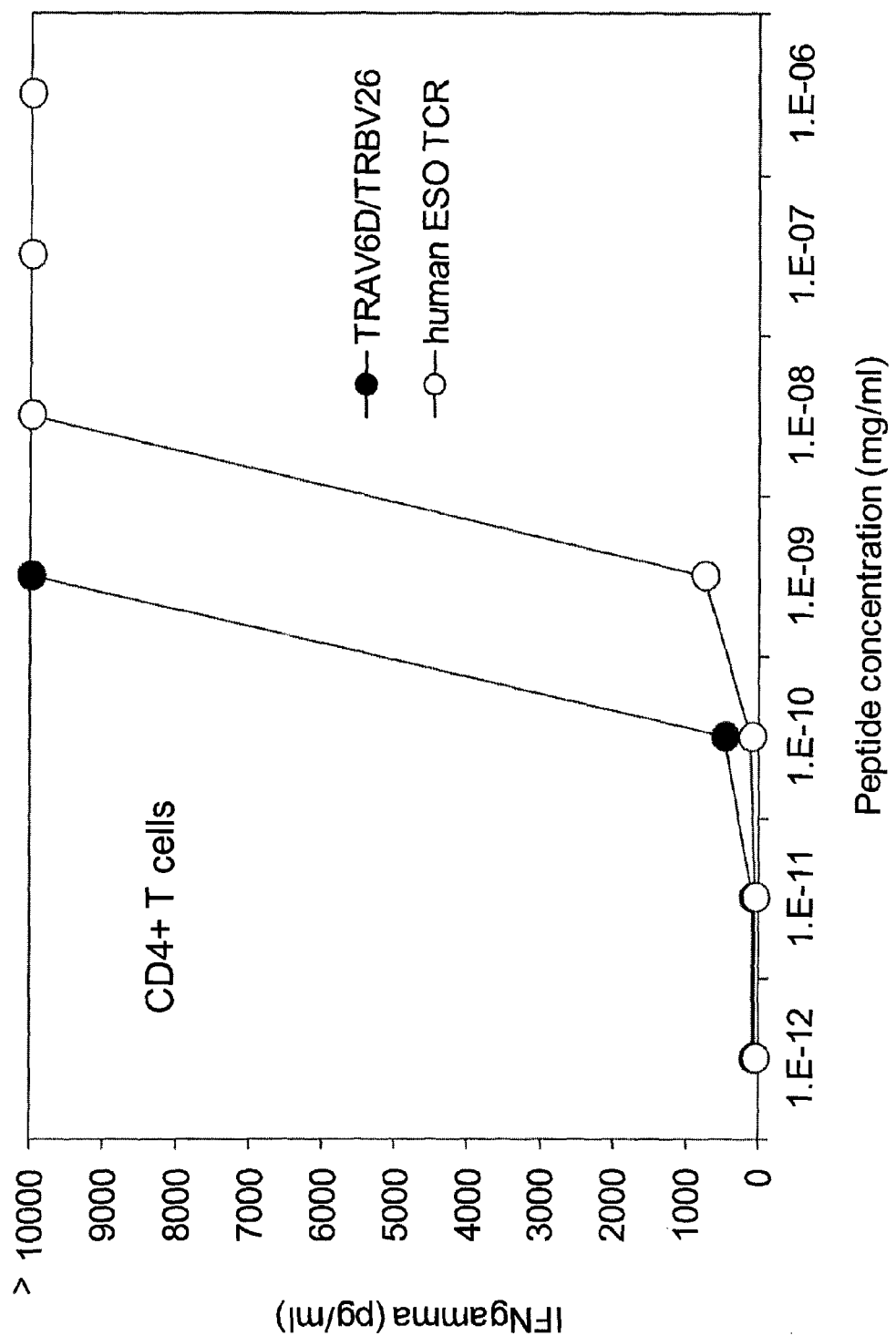

The invention provides an isolated or purified T-cell receptor (TCR) having antigenic specificity for NY-ESO-1 and comprising a murine variable region. NY-ESO-1 is a cancer testis antigen (CTA), which is expressed only in tumor cells and non-MHC expressing germ cells of the testis and placenta. NY-ESO-1 is expressed in a variety of human cancers including, but not limited to, melanoma, breast cancer, lung cancer, prostate cancer, thyroid cancer, ovarian cancer, and synovial cell sarcoma. The NY-ESO-1 protein may comprise, consist, or consist essentially of, SEQ ID NO: 1.

The TCR may have antigenic specificity for any NY-ESO-1 protein, polypeptide or peptide. In an embodiment of the invention, the TCR has antigenic specificity for a NY-ESO-1 protein comprising, consisting of, or consisting essentially of, SEQ ID NO: 1. In a preferred embodiment of the invention, the TCR has antigenic specificity for a NY-ESO-1 157-165 peptide comprising, consisting of, or consisting essentially of, SLLMWITQC (SEQ ID NO: 2).

The phrase "having antigenic specificity" as used herein means that the TCR can specifically bind to and immunologically recognize NY-ESO-1, such that binding of the TCR to NY-ESO-1 elicits an immune response.

In an embodiment of the invention, the inventive TCRs are able to recognize NY-ESO-1 in a major histocompatibility complex (MHC) class I-dependent manner. By "MHC class I-dependent manner" as used herein means that the TCR elicits an immune response upon binding to NY-ESO-1 within the context of an MHC class I molecule. The MHC class I molecule can be any MHC class I molecule known in the art, e.g., HLA-A molecules. In an embodiment of the invention, the MHC class I molecule is an HLA-A2 molecule.

In an embodiment of the invention, the inventive TCRs comprise a murine variable region. The inventive TCRs may further comprise a constant region derived from any suitable species such as, e.g., human or mouse. Preferably, the inventive TCRs further comprise a murine constant region. In an especially preferred embodiment, the inventive TCRs are murine TCRs comprising both a murine variable region and a murine constant region.

As used herein, the term "murine," when referring to a TCR or any component of a TCR described herein (e.g., complementarity determining region (CDR), variable region, constant region, alpha chain, and/or beta chain), means a TCR (or component thereof) which is derived from a mouse, i.e., a TCR (or component thereof) that originated from or was, at one time, expressed by a mouse T cell. Desirably, the TCR (or component thereof) is expressed on the surface of a human host cell.

The TCRs of the invention provide many advantages, including when used for adoptive cell transfer. For example, without being bound by a particular theory or mechanism, it is believed that because NY-ESO-1 is expressed by cells of multiple cancer types, the inventive TCRs advantageously provide the ability to destroy cells of multiple types of cancer and, accordingly, treat or prevent multiple types of cancer. Additionally, without being bound to a particular theory or mechanism, it is believed that because NY-ESO-1 is a cancer testis antigen that is expressed only in tumor cells and non-MHC expressing germ cells of the testis and placenta, the inventive TCRs advantageously target the destruction of cancer cells while minimizing or eliminating the destruction of normal, non-cancerous cells, thereby reducing, for example, minimizing or eliminating, toxicity. It is also believed that murine TCRs may provide increased expression (e.g., higher numbers of TCRs) on the surface of a human host cell and/or increased functionality (as measured by, e.g., cytokine release and cytotoxicity) as compared to a human TCR. Without being bound to a particular theory of mechanism, it is believed that the improved expression and/or functionality results from a reduction in the mixing of endogenous and exogenous (transduced) TCR chains in the host cell. Accordingly, it is believed that murine TCRs can replace endogenous TCRs on the surface of a human host cell more effectively than an exogenous human TCR. It is also believed that murine TCRs provide improved pairing of TCR chains and/or improved interactions with the CD3 complex of the human host cell as compared to exogenous human TCRs expressed by a human host cell.

An embodiment of the invention provides a TCR comprising two polypeptides (i.e., polypeptide chains), such as an α chain of a TCR, a β chain of a TCR, a γ chain of a TCR, a δ chain of a TCR, or a combination thereof. The polypeptides of the inventive TCR can comprise any amino acid sequence, provided that the TCR has antigenic specificity for NY-ESO-1 and comprises a murine variable region.

In a preferred embodiment of the invention, the TCR comprises two polypeptide chains, each of which comprises a variable region comprising a complementarity determining region (CDR) 1, a CDR2, and a CDR3 of a TCR. Preferably, the first polypeptide chain comprises a CDR1 comprising the amino acid sequence of SEQ ID NO: 3 (CDR1 of α chain), a CDR2 comprising the amino acid sequence of SEQ ID NO: 4 (CDR2 of α chain), and a CDR3 comprising the amino acid sequence of SEQ ID NO: 5 (CDR3 of α chain), and the second polypeptide chain comprises a CDR1 comprising the amino acid sequence of SEQ ID NO: 6 (CDR1 of β chain), a CDR2 comprising the amino acid sequence of SEQ ID NO: 7 (CDR2 of β chain), and a CDR3 comprising the amino acid sequence of SEQ ID NO: 8 (CDR3 of β chain). In this regard, the inventive TCR can comprise the amino acid sequences selected from the group consisting of SEQ ID NOs: 3-5, 6-8, and 3-8. Preferably the TCR comprises the amino acid sequences of SEQ ID NOs: 3-8.

Alternatively or additionally, the TCR can comprise an amino acid sequence of a variable region of a TCR comprising the CDRs set forth above. In this regard, the TCR can comprise the amino acid sequence of SEQ ID NO: 9 (the variable region of an α chain) or 10 (the variable region of a β chain), or both SEQ ID NOs: 9 and 10. Preferably, the inventive TCR comprises the amino acid sequences of SEQ ID NOs: 9 and 10.

Alternatively or additionally, the TCR can comprise an α chain of a TCR and a β chain of a TCR. Each of the α chain and β chain of the inventive TCR can independently comprise any amino acid sequence. Preferably, the α chain comprises the variable region of an α chain as set forth above. In this regard, the inventive TCR can comprise the amino acid sequence of SEQ ID NO: 11. An inventive TCR of this type can be paired with any β chain of a TCR. Preferably, the β chain of the inventive TCR comprises the variable region of a β chain as set forth above. In this regard, the inventive TCR can comprise the amino acid sequence of SEQ ID NO: 12. The inventive TCR, therefore, can comprise the amino acid sequence of SEQ ID NO: 11 or 12, or both SEQ ID NOs: 11 and 12. Preferably, the inventive TCR comprises the amino acid sequences of SEQ ID NOs: 11 and 12.

Also provided by the invention is an isolated or purified polypeptide comprising a functional portion of any of the TCRs described herein. The term "polypeptide" as used herein includes oligopeptides and refers to a single chain of amino acids connected by one or more peptide bonds.

With respect to the inventive polypeptides, the functional portion can be any portion comprising contiguous amino acids of the TCR of which it is a part, provided that the functional portion specifically binds to NY-ESO-1. The term "functional portion" when used in reference to a TCR refers to any part or fragment of the TCR of the invention, which part or fragment retains the biological activity of the TCR of which it is a part (the parent TCR). Functional portions encompass, for example, those parts of a TCR that retain the ability to specifically bind to NY-ESO-1, or detect, treat, or prevent cancer, to a similar extent, the same extent, or to a higher extent, as the parent TCR. In reference to the parent TCR, the functional portion can comprise, for instance, about 10%, 25%, 30%, 50%, 68%, 80%, 90%, 95%, or more, of the parent TCR.

The functional portion can comprise additional amino acids at the amino or carboxy terminus of the portion, or at both termini, which additional amino acids are not found in the amino acid sequence of the parent TCR. Desirably, the additional amino acids do not interfere with the biological function of the functional portion, e.g., specifically binding to NY-ESO-1, having the ability to detect cancer, treat or prevent cancer, etc. More desirably, the additional amino acids enhance the biological activity, as compared to the biological activity of the parent TCR.

The polypeptide can comprise a functional portion of either or both of the α and β chains of the TCRs of the invention, such as a functional portion comprising one or more of CDR1, CDR2, and CDR3 of the variable region(s) of the α chain and/or β chain of a TCR of the invention. In this regard, the polypeptide can comprise a functional portion comprising the amino acid sequence of SEQ ID NO: 3 (CDR1 of α chain), 4 (CDR2 of α chain), 5 (CDR3 of α chain), 6 (CDR1 of β chain), 7 (CDR2 of β chain), 8 (CDR3 of β chain), or a combination thereof. Preferably, the inventive polypeptide comprises a functional portion comprising SEQ ID NOs: 3-5, 6-8, or all of SEQ ID NOs: 3-8. More preferably, the polypeptide comprises a functional portion comprising the amino acid sequences of SEQ ID NOs: 3-8.

Alternatively or additionally, the inventive polypeptide can comprise, for instance, the variable region of the inventive TCR comprising a combination of the CDR regions set forth above. In this regard, the TCR can comprise the amino acid sequence of SEQ ID NO: 9 (the variable region of an α chain) or 10 (the variable region of a β chain), or both SEQ ID NOs: 9 and 10. Preferably, the polypeptide comprises the amino acid sequences of SEQ ID NOs: 9 and 10.

Alternatively or additionally, the inventive polypeptide can comprise the entire length of an α or β chain of one of the TCRs described herein. In this regard, the inventive polypeptide can comprise an amino acid sequence of SEQ ID NO: 11 or 12. Alternatively, the polypeptide of the invention can comprise both chains of the TCRs described herein. For example, the inventive polypeptide can comprise both amino acid sequences of SEQ ID NOs: 11 and 12.

The invention further provides an isolated or purified protein comprising at least one of the polypeptides described herein. By "protein" is meant a molecule comprising one or more polypeptide chains.

The protein of the invention can comprise a first polypeptide chain comprising the amino acid sequence of SEQ ID NO: 9 and a second polypeptide chain comprising the amino acid sequence of SEQ ID NO: 10. The protein of the invention can, for example, comprise a first polypeptide chain comprising the amino acid sequence of SEQ ID NO: 11 and a second polypeptide chain comprising the amino acid sequence of SEQ ID NO: 12. In this instance, the protein of the invention can be a TCR. Alternatively, if, for example, the protein comprises a single polypeptide chain comprising SEQ ID NO: 11 and SEQ ID NO: 12, or if the first and/or second polypeptide chain(s) of the protein further comprise(s) other amino acid sequences, e.g., an amino acid sequence encoding an immunoglobulin or a portion thereof, then the inventive protein can be a fusion protein. In this regard, the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof, including, but not limited to an immunoglobulin, CD3, CD4, CD8, an MHC molecule, a CD1 molecule, e.g., CD1a, CD1b, CD1c, CD1d, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods. See, for instance, Choi et al., *Mol. Biotechnol.* 31: 193-202 (2005).

In some embodiments of the invention, the TCRs, polypeptides, and proteins of the invention (including functional portions and functional variants) may be expressed as a single protein comprising a linker peptide linking the α chain and the β chain. Any linker peptide suitable for linking the α chain and the β chain may be used in the TCRs, polypeptides, and proteins (including functional portions and functional variants) of the invention. In an embodiment of the invention, the linker peptide is a picornavirus 2A peptide. In this regard, the TCRs, polypeptides, and proteins of the invention (including functional portions and functional variants) may further comprise a linker peptide comprising an amino acid sequence comprising SEQ ID NO: 13. The linker peptide may advantageously facilitate the expression of a recombinant TCR, polypeptide, and/or protein in a host cell. Upon expression of the construct including the linker peptide by a host cell, the linker peptide may be cleaved, resulting in separated α and β chains.

The protein of the invention can be a recombinant antibody comprising at least one of the inventive polypeptides described herein. As used herein, "recombinant antibody" refers to a recombinant (e.g., genetically engineered) protein comprising at least one of the polypeptides of the invention and a polypeptide chain of an antibody, or a portion thereof. The polypeptide of an antibody, or portion thereof, can be a heavy chain, a light chain, a variable or constant region of a heavy or light chain, a single chain variable fragment (scFv), or an Fc, Fab, or F(ab)$_2$' fragment of an antibody, etc. The polypeptide chain of an antibody, or portion thereof, can exist as a separate polypeptide of the recombinant antibody. Alternatively, the polypeptide chain of an antibody, or portion thereof, can exist as a polypeptide, which is expressed in frame (in tandem) with the polypeptide of the invention. The polypeptide of an antibody, or portion thereof, can be a polypeptide of any antibody or any antibody fragment, including any of the antibodies and antibody fragments described herein.

Included in the scope of the invention are functional variants of the inventive TCRs, polypeptides, and proteins described herein. The term "functional variant" as used herein refers to a TCR, polypeptide, or protein having substantial or significant sequence identity or similarity to a parent TCR, polypeptide, or protein, which functional variant retains the biological activity of the TCR, polypeptide, or protein of which it is a variant. Functional variants encompass, for example, those variants of the TCR, polypeptide, or protein described herein (the parent TCR, polypeptide, or protein) that retain the ability to specifically bind to NY-ESO-1 to a similar extent, the same extent, or to a higher extent, as the parent TCR, polypeptide, or protein. In reference to the parent TCR, polypeptide, or protein, the functional variant can, for instance, be at least about 30%, 50%, 75%, 80%, 90%, 91%, 92%, 93%, 94%, 95%, 96%, 97%, 98%, 99% or more identical in amino acid sequence to the parent TCR, polypeptide, or protein.

The functional variant can, for example, comprise the amino acid sequence of the parent TCR, polypeptide, or protein with at least one conservative amino acid substitution. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Alternatively or additionally, the functional variants can comprise the amino acid sequence of the parent TCR, polypeptide, or protein with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent TCR, polypeptide, or protein.

The TCR, polypeptide, or protein can consist essentially of the specified amino acid sequence or sequences described herein, such that other components of the functional variant, e.g., other amino acids, do not materially change the biological activity of the functional variant. In this regard, the inventive TCR, polypeptide, or protein can, for example, consist essentially of the amino acid sequence of SEQ ID NO: 11 or 12, or both SEQ ID NOs: 11 and 12. Also, for instance, the inventive TCRs, polypeptides, or proteins can consist essentially of the amino acid sequence(s) of SEQ ID NO: 9 or 10, or both SEQ ID NOs: 9 and 10. Furthermore, the inventive TCRs, polypeptides, or proteins can consist essentially of the amino acid sequence of SEQ ID NO: 3 (CDR1 of α chain), 4 (CDR2 of α chain), 5 (CDR3 of α chain), 6 (CDR1 of β chain), 7 (CDR2 of β chain), 8 (CDR3 of β chain), or any combination thereof, e.g., SEQ ID NOs: 3-5, 6-8, or 3-8.

The TCRs, polypeptides, and proteins of the invention (including functional portions and functional variants) can be of any length, i.e., can comprise any number of amino acids, provided that the TCRs, polypeptides, or proteins (or functional portions or functional variants thereof) retain their biological activity, e.g., the ability to specifically bind to NY-ESO-1, detect cancer in a mammal, or treat or prevent cancer in a mammal, etc. For example, the polypeptide can be 50 to 5000 amino acids long, such as 50, 70, 75, 100, 125, 150, 175, 200, 300, 400, 500, 600, 700, 800, 900, 1000 or more amino acids in length. In this regard, the polypeptides of the invention also include oligopeptides.

The TCRs, polypeptides, and proteins of the invention (including functional portions and functional variants) of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The TCRs, polypeptides, and proteins of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

When the TCRs, polypeptides, and proteins of the invention (including functional portions and functional variants) are in the form of a salt, preferably, the polypeptides are in the form of a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

The TCR, polypeptide, and/or protein of the invention (including functional portions and functional variants thereof) can be obtained by methods known in the art. Suitable methods of de novo synthesizing polypeptides and proteins are described in references, such as Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwood et al., Oxford University Press, Oxford, United Kingdom, 2000; and U.S. Pat. No. 5,449,752. Also, polypeptides and proteins can be recombinantly produced using the nucleic acids described herein using standard recombinant methods. See, for instance, Sambrook et al., *Molecular Cloning: A Laboratory Manual*, 3$^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994. Further, some of the TCRs, polypeptides, and proteins of the invention (including functional portions and functional variants thereof) can be isolated and/or purified from a source, such as a plant, a bacterium, an insect, a mammal, e.g., a mouse, a human, etc. Methods of isolation and purification are well-known in the art. Alternatively, the TCRs, polypeptides, and/or proteins described herein (including functional portions and functional variants thereof) can be commercially synthesized by companies, such as Synpep (Dublin, Calif.), Peptide Technologies Corp. (Gaithersburg, Md.), and Multiple Peptide Systems (San Diego, Calif.). In this respect, the inventive TCRs, polypeptides, and proteins can be synthetic, recombinant, isolated, and/or purified.

Included in the scope of the invention are conjugates, e.g., bioconjugates, comprising any of the inventive TCRs, polypeptides, or proteins (including any of the functional portions or variants thereof), nucleic acids, recombinant expression vectors, host cells, populations of host cells, or antibodies, or antigen binding portions thereof. Conjugates, as well as methods of synthesizing conjugates in general, are known in the art (See, for instance, Hudecz, F., *Methods Mol. Biol.* 298: 209-223 (2005) and Kirin et al., *Inorg Chem.* 44(15): 5405-5415 (2005)).

Further provided by the invention is a nucleic acid comprising a nucleotide sequence encoding any of the TCRs, polypeptides, or proteins described herein (including functional portions and functional variants thereof).

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i)

above. For purposes herein, the replication can be in vitro replication or in vivo replication.

The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl)uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acid can comprise any nucleotide sequence which encodes any of the inventive TCRs, polypeptides, or proteins, or functional portions or functional variants thereof. For example, the nucleic acid can comprise a nucleotide sequence comprising, consisting of, or consisting essentially of SEQ ID NO: 19 (wild-type α chain) or SEQ ID NO: 20 (wild-type β chain) or both SEQ ID NOs: 19 and 20.

In some embodiments, the nucleotide sequence may be codon-optimized. Without being bound to a particular theory or mechanism, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency. In an embodiment of the invention, the codon-optimized nucleotide sequence may comprise, consist, or consist essentially of SEQ ID NO: 15 (codon-optimized α chain), SEQ ID NO: 16 (codon-optimized β chain), SEQ ID NO: 21 (codon-optimized variable region of α chain), SEQ ID NO: 22 (codon-optimized variable region of β chain), both SEQ ID NOs: 15 and 16, both SEQ ID NOs: 21 and 22, both SEQ ID NOs: 15 and 20, or both SEQ ID NOs: 16 and 19.

In an embodiment of the invention, the nucleotide sequence encoding the TCRs, polypeptides, and proteins of the invention (including functional portions and functional variants thereof) may further comprise a nucleotide sequence encoding any of the linker peptides described herein with respect to other aspects of the invention. In an embodiment of the invention, the linker peptide may be encoded by a nucleotide sequence comprising SEQ ID NO: 14.

The invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

The nucleotide sequence alternatively can comprise a nucleotide sequence which is degenerate to SEQ ID NO: 15, SEQ ID NO: 16, SEQ ID NO: 19, SEQ ID NO: 20, SEQ ID NO: 21, SEQ ID NO: 22, both SEQ ID NOs: 15 and 16, both SEQ ID NOs: 19 and 20, both SEQ ID NOs: 21 and 22, both SEQ ID NOs: 15 and 20, or both SEQ ID NOs: 16 and 19. Preferably, the nucleic acid comprises a nucleotide sequence comprising SEQ ID NO: 15, 16, 19, 20, 21, or 22, SEQ ID NOs: 15 and 16, SEQ ID NOs: 19 and 20, SEQ ID NOs: 21 and 22, SEQ ID NOs: 15 and 20, or SEQ ID NOs: 16 and 19, or a nucleotide sequence which is degenerate thereto.

The invention also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive TCRs. It is generally appreciated that conditions can be rendered more stringent by the addition of increasing amounts of formamide.

The nucleic acids of the invention can be incorporated into a recombinant expression vector. In this regard, the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages do not hinder the transcription or replication of the vector.

The recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM and pMAMneo (Clontech). Preferably, the recombinant expression vector is a viral vector, e.g., a retroviral vector or a lentiviral vector.

The recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papilloma virus, and the like.

Desirably, the recombinant expression vector comprises regulatory sequences, such as transcription and translation initiation and termination codons, which are specific to the type of host cell (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the TCR, polypeptide, or protein (including functional portions and functional variants thereof), or to the nucleotide sequence which is complementary to or which hybridizes to the nucleotide sequence encoding the TCR, polypeptide, or protein. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression. Further, the recombinant expression vectors can be made to include a suicide gene.

As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, *Suicide Gene Therapy: Methods and Reviews*, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

The inventive recombinant expression vectors may comprise a nucleotide sequence encoding all or a portion of the alpha chain positioned 5' of the nucleotide sequence encoding all or a portion of the beta chain. In this regard, an embodiment of the invention provides a recombinant expression vector comprising a nucleotide sequence encoding a CDR 1α, CDR2α, CDR3α, CDR1β, CDR2β, and CDR3β, and the nucleotide sequence encoding the CDR1α, CDR2α, and CDR3α is 5' of the nucleotide sequence encoding the CDR1β, CDR2β, and CDR3β. Likewise, the nucleotide sequence encoding the CDR1β, CDR2β, and CDR3β may be 3' of the nucleotide sequence encoding the CDR1α, CDR2α, and CDR3α. In another embodiment of the invention, the recombinant expression vector comprises a nucleotide sequence encoding a variable region of the alpha chain and a variable region of the beta chain, and the nucleotide sequence encoding the variable region of the alpha chain is 5' of the nucleotide sequence encoding the variable region of the beta chain. Likewise, the nucleotide sequence encoding the variable region of the beta chain may be 3' of the nucleotide sequence encoding the variable region of the alpha chain. In still another embodiment of the invention, the recombinant expression vector comprises a nucleotide sequence encoding an alpha chain and a beta chain, and the nucleotide sequence encoding the alpha chain is 5' of the nucleotide sequence encoding the beta chain. Likewise, the nucleotide sequence encoding the beta chain may be 3' of the nucleotide sequence encoding the alpha chain. The recombinant expression vector comprising a nucleotide sequence encoding all or a portion of the alpha chain positioned 5' of the nucleotide sequence encoding all or a portion of the beta chain may comprise SEQ ID NO: 17.

The inventive recombinant expression vectors may comprise a nucleotide sequence encoding all or a portion of the alpha chain positioned 3' of the nucleotide sequence encoding all or a portion of the beta chain. Without being bound by a particular theory or mechanism, it is believed that a TCR, polypeptide, or protein (or functional portion or variant thereof) encoded by a recombinant expression vector in which the nucleotide sequence encoding all or a portion of the alpha chain is positioned 3' of the nucleotide sequence encoding all or a portion of the beta chain provides improved functionality and antigen recognition as compared to a TCR, polypeptide, or protein (or functional portion or functional variant thereof) encoded by a recombinant expression vector in which the nucleotide sequence encoding all or a portion of the alpha chain is positioned 5' of the nucleotide sequence encoding all or a portion of the beta chain. In this regard, an embodiment of the invention provides a recombinant expression vector comprising a nucleotide sequence encoding a CDR 1α, CDR2α, CDR3α, CDR1β, CDR2β, and CDR3β, and the nucleotide sequence encoding the CDR1α, CDR2α, and CDR3α is 3' of the nucleotide sequence encoding the CDR1β, CDR2β, and CDR3β. Likewise, the nucleotide sequence encoding the CDR1β, CDR2β, and CDR3β may be 5' of the nucleotide sequence encoding the CDR1α, CDR2α, and CDR3α. In another embodiment of the invention, the recombinant expression vector comprises a nucleotide sequence encoding a variable region of the alpha chain and a variable region of the beta chain, and the nucleotide sequence encoding the variable region of the alpha chain is 3' of the nucleotide sequence encoding the variable region of the beta chain. Likewise, the nucleotide sequence encoding the variable region of the beta chain may be 5' of the nucleotide sequence encoding the variable region of the alpha chain. In still another embodiment of the invention, the recombinant expression vector comprises a nucleotide sequence encoding an alpha chain and a beta chain, and the nucleotide sequence encoding the alpha chain is 3' of the nucleotide sequence encoding the beta chain. Likewise, the nucleotide sequence encoding the beta chain may be 5' of the nucleotide sequence encoding the alpha chain. The recombinant expression vector comprising a nucleotide sequence encoding all or a portion of the alpha chain positioned 3' of the nucleotide sequence encoding all or a portion of the beta chain may comprise SEQ ID NO: 18.

In an embodiment of the invention, the recombinant expression vector may comprise a DNA tag. The DNA tag may distinguish the recombinant expression vector from another vector encoding the same protein sequence. The DNA tag may not be included within the nucleotide sequence encoding the inventive TCR (including functional portions and functional variants thereof), polypeptide, or protein and, therefore, may not affect its expression. Recombinant expression vectors including the DNA tag make it possible to put the same nucleotide sequence into several different cell populations and subsequently distinguish between those populations based on which vector they contain.

The invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α $E.$ $coli$ cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5α cell. For purposes of producing a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell may be a peripheral blood lymphocyte (PBL) or a peripheral blood mononuclear cell (PBMC). Preferably, the host cell may be a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, $CD4^+/CD8^+$ double positive T cells, $CD4^+$ helper T cells, e.g., $Th_1$ and $Th_2$ cells, $CD8^+$ T cells, cytotoxic T cells, tumor infiltrating lymphocyte cells, memory T cells, naïve T cells, and the like. Preferably, the T cell may be a $CD8^+$ T cell or a $CD4^+$ T cell.

Also provided by the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

The invention further provides an antibody, or antigen binding portion thereof, which specifically binds to a functional portion of any of the TCRs described herein. Preferably, the functional portion specifically binds to NY-ESO-1, e.g., the functional portion comprising the amino acid sequence SEQ ID NO: 3 (CDR1 of α chain), 4 (CDR2 of α chain), 5 (CDR3 of α chain), 6 (CDR1 of β chain), 7 (CDR2 of β chain), 8 (CDR3 of β chain), SEQ ID NO: 9, SEQ ID NO: 10, or a combination thereof, e.g., 3-5, 6-8, 3-8, or 9-10. More preferably, the functional portion comprises the amino acid sequences of SEQ ID NOs: 3-8. In a preferred embodiment, the antibody, or antigen binding portion thereof, binds to an epitope which is formed by all 6 CDRs (CDR1-3 of the alpha chain and CDR1-3 of the beta chain). The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for the functional portion of the inventive TCR. Desirably, the antibody is specific for the functional portion of the inventive TCR, such that there is minimal cross-reaction with other peptides or proteins.

Methods of testing antibodies for the ability to bind to any functional portion of the inventive TCR are known in the art and include any antibody-antigen binding assay, such as, for example, radioimmunoassay (RIA), ELISA, Western blot, immunoprecipitation, and competitive inhibition assays (see, e.g., Janeway et al., infra).

Suitable methods of making antibodies are known in the art. For instance, standard hybridoma methods are described in, e.g., Köhler and Milstein, *Eur. J.* Immunol., 5, 511-519 (1976), Harlow and Lane (eds.), *Antibodies: A Laboratory Manual*, CSH Press (1988), and C. A. Janeway et al. (eds.), *Immunobiology*, 5$^{th}$ Ed., Garland Publishing, New York, N.Y. (2001)). Alternatively, other methods, such as EBV-hybridoma methods (Haskard and Archer, *J. Immunol. Methods*, 74(2), 361-67 (1984), and Roder et al., *Methods Enzymol.*, 121, 140-67 (1986)), and bacteriophage vector expression systems (see, e.g., Huse et al., *Science*, 246, 1275-81 (1989)) are known in the art. Further, methods of producing antibodies in non-human animals are described in, e.g., U.S. Pat. Nos. 5,545,806, 5,569,825, and 5,714,352).

Phage display furthermore can be used to generate the antibody of the invention. In this regard, phage libraries encoding antigen-binding variable (V) domains of antibodies can be generated using standard molecular biology and recombinant DNA techniques (see, e.g., Sambrook et al. (eds.), *Molecular Cloning, A Laboratory Manual*, 3$^{rd}$ Edition, Cold Spring Harbor Laboratory Press, New York (2001)). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., *J. Mol. Biol.*, 235, 959-973 (1994).

The invention also provides antigen binding portions of any of the antibodies described herein. The antigen binding portion can be any portion that has at least one antigen binding site, such as Fab, F(ab')$_2$, dsFv, sFv, diabodies, and triabodies.

A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., *Protein Engineering*, 7, 697-704 (1994)). Antibody fragments of the invention, however, are not limited to these exemplary types of antibody fragments.

Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

The inventive TCRs, polypeptides, proteins, (including functional portions and functional variants thereof), nucleic acids, recombinant expression vectors, host cells (including populations thereof), and antibodies (including antigen binding portions thereof), can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70% or 80%, or can be 100%.

The inventive TCRs, polypeptides, proteins (including functional portions and variants thereof), nucleic acids, recombinant expression vectors, host cells (including populations thereof), and antibodies (including antigen binding portions thereof), all of which are collectively referred to as "inventive TCR materials" hereinafter, can be formulated into a composition, such as a pharmaceutical composition. In this regard, the invention provides a pharmaceutical composition comprising any of the TCRs, polypeptides, proteins, functional portions, functional variants, nucleic acids, expression vectors, host cells (including populations thereof), and antibodies (including antigen binding portions thereof), and a pharmaceutically acceptable carrier. The inventive pharmaceutical compositions containing any of the inventive TCR materials can comprise more than one inventive TCR material, e.g., a polypeptide and a nucleic acid, or two or more different TCRs. Alternatively, the pharmaceutical composition can comprise an inventive TCR material in combination with another pharmaceutically active agents or drugs, such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used and is limited only by chemico-physical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular inventive TCR material, as well as by the particular method used to administer the inventive TCR material. Accordingly, there are a variety of suitable formulations of the pharmaceutical composition of the invention. The following formulations for parenteral, subcutaneous, intravenous, intramuscular, intraarterial, intrathecal, and interperitoneal administration are exemplary and are in no way limiting. More than one route can be used to administer the inventive TCR materials, and in certain instances, a particular route can provide a more immediate and more effective response than another route.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The inventive TCR material can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1,3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the inventive TCR material in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Toissel, 4th ed., pages 622-630 (1986)). Preferably, when administering cells, e.g., dendritic cells, the cells are administered via injection.

It will be appreciated by one of skill in the art that, in addition to the above-described pharmaceutical compositions, the inventive TCR materials of the invention can be formulated as inclusion complexes, such as cyclodextrin inclusion complexes, or liposomes.

For purposes of the invention, the amount or dose of the inventive TCR material administered should be sufficient to effect, e.g., a therapeutic or prophylactic response, in the subject or animal over a reasonable time frame. For example, the dose of the inventive TCR material should be sufficient to bind to NY-ESO-1, or detect, treat or prevent cancer in a period of from about 2 hours or longer, e.g., 12 to 24 or more hours, from the time of administration. In certain embodiments, the time period could be even longer. The dose will be determined by the efficacy of the particular inventive TCR material and the condition of the animal (e.g., human), as well as the body weight of the animal (e.g., human) to be treated.

Many assays for determining an administered dose are known in the art. For purposes of the invention, an assay, which comprises comparing the extent to which target cells are lysed or IFN-γ is secreted by T cells expressing the inventive TCR, polypeptide, or protein upon administration of a given dose of such T cells to a mammal among a set of mammals of which is each given a different dose of the T cells, could be used to determine a starting dose to be administered to a mammal. The extent to which target cells are lysed or IFN-γ is secreted upon administration of a certain dose can be assayed by methods known in the art, including, for instance, the methods described herein as Example 3.

The dose of the inventive TCR material also will be determined by the existence, nature and extent of any adverse side effects that might accompany the administration of a particular inventive TCR material. Typically, the attending physician will decide the dosage of the inventive TCR material with which to treat each individual patient, taking into consideration a variety of factors, such as age, body weight, general health, diet, sex, inventive TCR material to be administered, route of administration, and the severity of the condition being treated. By way of example and not intending to limit the invention, the dose of the inventive TCR material can be about 0.001 to about 1000 mg/kg body weight of the subject being treated/day, from about 0.01 to about 10 mg/kg body weight/day, about 0.01 mg to about 1 mg/kg body weight/day.

One of ordinary skill in the art will readily appreciate that the inventive TCR materials of the invention can be modified in any number of ways, such that the therapeutic or prophylactic efficacy of the inventive TCR materials is increased through the modification. For instance, the inventive TCR materials can be conjugated either directly or indirectly through a bridge to a targeting moiety. The practice of conjugating compounds, e.g., inventive TCR materials, to targeting moieties is known in the art. See, for instance, Wadwa et al., *J. Drug Targeting* 3: 111 (1995) and U.S. Pat. No. 5,087,616. The term "targeting moiety" as used herein, refers to any molecule or agent that specifically recognizes and binds to a cell-surface receptor, such that the targeting moiety directs the delivery of the inventive TCR materials to a population of cells on which surface the receptor is expressed. Targeting moieties include, but are not limited to, antibodies, or fragments thereof, peptides, hormones, growth factors, cytokines, and any other natural or non-natural ligands, which bind to cell surface receptors (e.g., Epithelial Growth Factor Receptor (EGFR), T-cell receptor (TCR), B-cell receptor (BCR), CD28, Platelet-derived Growth Factor Receptor (PDGF), nicotinic acetylcholine receptor (nAChR), etc.). The term "bridge" as used herein, refers to any agent or molecule that bridges the inventive TCR materials to the targeting moiety. One of ordinary skill in the art recognizes that sites on the inventive TCR materials, which are not necessary for the function of the inventive TCR materials, are ideal sites for attaching a bridge and/or a targeting moiety, provided that the bridge and/or targeting moiety, once attached to the inventive TCR materials, do(es) not interfere with the function of the inventive TCR materials, i.e., the ability to bind to NY-ESO-1, or to detect, treat, or prevent cancer.

Alternatively, the inventive TCR materials can be modified into a depot form, such that the manner in which the inventive TCR materials is released into the body to which it is administered is controlled with respect to time and location within the body (see, for example, U.S. Pat. No. 4,450,150). Depot forms of inventive TCR materials can be, for example, an implantable composition comprising the inventive TCR materials and a porous or non-porous material, such as a polymer, wherein the inventive TCR materials is encapsulated by or diffused throughout the material and/or degradation of the non-porous material. The depot is then implanted into the desired location within the body and the inventive TCR materials are released from the implant at a predetermined rate.

It is contemplated that the inventive pharmaceutical compositions, TCRs (including functional portions or variants thereof), polypeptides, proteins, nucleic acids, recombinant expression vectors, host cells, or populations of cells can be used in methods of treating or preventing cancer. Without being bound to a particular theory or mechanism, the inventive TCRs are believed to bind specifically to NY-ESO-1, such that the TCR (or related inventive polypeptide or protein, or functional portion or variant thereof) when expressed by a cell is able to mediate an immune response against the cell expressing NY-ESO-1. In this regard, the invention provides a method of treating or preventing cancer in a mammal, comprising administering to the mammal any of the TCRs, polypeptides, or proteins described herein, any nucleic acid or recombinant expression vector comprising a nucleotide sequence encoding any of the TCRs, polypeptides, proteins described herein, or any host cell or population of cells comprising a recombinant vector which encodes any of the TCRs, polypeptides, or proteins described herein, in an amount effective to treat or prevent cancer in the mammal.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

Also provided is a method of detecting the presence of cancer in a mammal. The method comprises (i) contacting a sample comprising cells of the cancer any of the inventive TCRs, polypeptides, proteins, nucleic acids, recombinant expression vectors, host cells, populations of cells, or antibodies, or antigen binding portions thereof, described herein, thereby forming a complex, and detecting the complex, wherein detection of the complex is indicative of the presence of cancer in the mammal.

With respect to the inventive method of detecting cancer in a mammal, the sample of cells of the cancer can be a sample comprising whole cells, lysates thereof, or a fraction of the whole cell lysates, e.g., a nuclear or cytoplasmic fraction, a whole protein fraction, or a nucleic acid fraction.

For purposes of the inventive detecting method, contacting can take place in vitro or in vivo with respect to the mammal. Preferably, the contacting is in vitro.

Also, detection of the complex can occur through any number of ways known in the art. For instance, the inventive TCRs, polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

For purposes of the inventive methods, wherein host cells or populations of cells are administered, the cells can be cells that are allogeneic or autologous to the mammal. Preferably, the cells are autologous to the mammal.

With respect to the inventive methods, the cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor. Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, synovial cell sarcoma, testicular cancer, thyroid cancer, ureter cancer, and urinary bladder cancer. Preferably, the cancer is melanoma, breast cancer, lung cancer, prostate cancer, thyroid cancer, ovarian cancer, or synovial cell sarcoma.

The mammal referred to in the inventive methods can be any mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

EXAMPLES

The following examples further illustrate the invention but, of course, should not be construed as in any way limiting its scope.

Cell Lines

Melanoma lines 1300mel (NY-ESO-1+, HLA-A2+), 624.38mel (NY-ESO-1+, HLA-A2+), A375mel (NY-ESO-1+, HLA-A2+), 938mel (NY-ESO-1+, HLA-A2−), 888mel (NY-ESO-1−, HLA-A2−), SK23mel (NY-ESO-1−, HLA-A2+), 1359mel (NY-ESO-1+, HLA-A2−), 1359-A2mel (NY-ESO-1+, HLA-A2+), 624mel (NY-ESO-1+, HLA-A2+), and 1390mel (NY-ESO-1+, HLA-A2+), were generated from resected tumor lesions and were cultured in R10 medium consisting of RPMI 1640 supplemented with 10% fetal bovine serum, 2 mmol/L L-glutamine, 50 units/mL penicillin, and 50 μg/mL (Invitrogen) and 25 mmol/L HEPES (GIBCO, Invitrogen). Other cell lines used included: the cervical cancer cell line Caski (NY-ESO-1+, HLA-A2+), (ATCC CRL-1550) the osteosarcoma cell line Saos2 (NY-ESO-1+, HLA-A2+), (ATCC HTB-85), and the neuroblastoma cell line SK NAS-A2 (NY-ESO-1+, HLA-A2+), (ATCC CRL-2137), the non-small cell lung cancer cell line H1299A2 (NY-ESO-1+, HLA-A2+), the breast carcinoma cell line MDA-MB-435S-A2 (NY-ESO-1+, HLA-A2+), (ATCC® HTB-129), all three of which were transduced with retroviral construct to express HLA-A*0201 (Navuaux et al., *J. Virol.*, 70: 5701-05 (1996), Parkhurst et al., *Clin. Cancer Res.*, 15: 169-180 (2009), Robbins et al., *J. Immunol.*, 180: 6116-31 (2008), Wargo et al., *Cancer Immunol. Immunother.*, 58: 394 (2009)), COS-A2-ESO, which was transduced with a retroviral vector expressing the NY-ESO-1 gene, and COS-A2-CEA, which was transduced with a retroviral vector expressing the CEA gene.

Example 1

This example demonstrates the identification of murine anti-NY-ESO-1 T cell clones.

HLA-A2 transgenic mice were immunized with 100 μg of peptide (NY-ESO-1$_{157-165}$) and 120 μg of helper peptide (hepatitis B virus core peptide (HBVc):128-140) in 100 μl Incomplete Freund's adjuvant (IFA) subcutaneously (s.c.) at the base of the tail (50 μg of NY-ESO-1$_{157-165}$ peptide on each of two sides of the tail), followed by a boost one week later with the same immunization.

Day 0: One week after the second immunization, splenocytes were harvested and stimulated in vitro with one of the following: (i) LPS-activated HLA-A2+ splenocytes (3,000 rads) ("LPS blast") pulsed with 1 μg/ml priming peptide and 10 μg/ml human β2-microgobulin or (ii) T2 cells (17,000 rads) pulsed with 1, 0.1 or 0.01 μg/ml peptide.

Day 7: Bulk cultures were evaluated for specific reactivity via IFNγ secretion upon co-culture with one of the tumor cell lines set forth in Table 1. The results are shown in Table 1 (IFN-γ (pg/ml) post 1 bulk stimulation; "nt"=not tested). Because cytokine release was sometimes very high in response to T2 cells loaded with the HBV peptide, the underlined values for tumor targets indicate twice the background values obtained with media alone and negative tumors, and the underlined values for peptides indicate twice background values obtained with T2 and HBV peptide.

TABLE 1

| | HLA-A2 | NY-ESO-1 | RNA copies per GAPDH (×100) | LPS blasts + 1 μg/ml peptide | T2 + 1 μg/ml peptide | T2 + 0.1 μg/ml peptide | T2 + 0.01 μg/ml peptide |
|---|---|---|---|---|---|---|---|
| T2 + HBV | + | − | nt | 41 | 266 | 200 | 71 |
| T2 + ESO: 157 | + | + | nt | 549 | 4505 | 4,464 | 406 |
| media | − | − | nt | 22 | 53 | 69 | 41 |
| 888mel | − | − | 0.02 | 36 | 133 | 110 | 88 |
| Sk23mel | + | − | 0.01 | 24 | 76 | 134 | 17 |
| 1359mel | − | + | 5.68 | 55 | 92 | 21 | 26 |
| 1359-A2 | + | + | nt | 22 | 98 | 73 | 48 |
| A375mel | + | + | 59.08 | 41 | 47 | 143 | 49 |
| 624mel | + | + | 4.14 | 41 | 73 | 200 | 22 |
| 1390mel | + | + | nt | — | — | — | — |
| 1363mel | + | + | nt | — | — | — | — |
| COS-A2-CEA | + | − | nt | 32 | 94 | 67 | 56 |
| COS-A2-ESO | + | + | nt | 33 | 92 | 65 | 61 |
| 293-A2-gp100 | + | − | nt | — | — | — | — |
| 293-A2-ESO | + | + | nt | — | — | — | — |

Day 11: Peptide/tumor reactive bulk cultures were cloned at 10 cells/well under the following conditions (10 plates per condition): (i) irradiated T2 cells (18,000 rads) pulsed with 1, 0.1, or 0.01 μg/ml peptide: 5×10$^4$ cells/well; (ii) irradiated C57BL/6 splenocyte feeders (3,000 rads): 5×10$^4$ cells/well; and (iii) 10 CU/ml IL-2.

Days 25-30: Growth positive wells were selected and restimulated in 48-well plates under the following conditions: (i) irradiated T2 cells (18,000 rads) pulsed with 1, 0.1, or 0.01 μg/ml peptide: 2×10$^5$ cells/well; (ii) irradiated C57BL/6 splenocyte feeders (3,000 rads): 1×10$^6$ cells/well; and (iii) 10 CU/ml IL-2.

Days 37-44: Clones were evaluated for specific reactivity via IFNγ secretion upon co-culture with the tumor cell lines set forth in Table 2. Tumor cells were treated with IFNγ (20 ng/ml) and tumor necrosis factor alpha (3 ng/ml) overnight prior to the assay.

The splenocytes stimulated with LPS-activated HLA-A2+ splenocytes (3,000 rads) pulsed with 1 μg/ml priming peptide and 10 μg/ml human β2-microgobulin on Day 0 produced 8 out of 960 growth positive wells. Data for the two most reactive clones are shown in Table 2 (post 1 bulk stimulation; IFN-γ (pg/ml)).

TABLE 2

| | HLA-A2 | NY-ESO-1 | RNA copies per GAPDH (×100) | B | H |
|---|---|---|---|---|---|
| T2 + HBV | + | − | nt | 393 | 283 |
| T2 + ESO: 157 | + | + | nt | >14,000 | >14,000 |
| media | − | − | nt | 404 | 292 |
| 888mel | − | − | 0.02 | 386 | 288 |
| Sk23mel | + | − | 0.01 | — | — |
| 1359mel | − | + | 5.68 | 354 | 285 |
| 1359-A2 | + | + | nt | 11,781 | 16,436 |
| A375mel | + | + | 59.08 | 383 | 1,954 |
| 624mel | + | + | 4.14 | 363 | 14,298 |
| 1390mel | + | + | nt | 288 | 17,567 |
| 1363mel | + | + | nt | 3,582 | — |
| COS-A2-CEA | + | − | nt | 348 | 289 |
| COS-A2-ESO | + | + | nt | >14,000 | >14,000 |
| 293-A2-gp100 | + | − | nt | 373 | 274 |
| 293-A2-ESO | + | + | nt | 335 | 8,813 |

Days 46-49: Clones of interest were restimulated in 24-well plates under the following conditions: (i) irradiated T2 cells (18,000 rads) pulsed with 1, 0.1, or 0.01 μg/ml peptide: 5×10⁵ cells/well; (ii) irradiated C57BL/6 splenocyte feeders (3,000 rads): 1×10⁶ cells/well; and (iii) 10 CU/ml IL-2. Restimulated clones were flash-frozen for RNA preparation.

Example 2

This example demonstrates the identification of murine anti-NY-ESO-1 T cell clones.

HLA-A2 transgenic mice were immunized and the splenocytes were harvested, stimulated, and evaluated for specific reactivity as described in Example 1.

Day 11: The bulk cultures were restimulated in 24-well plates under the following conditions: (i) irradiated T2 cells (18,000 rads) pulsed with 1, 0.1, or 0.01 μg/ml peptide: 4×10⁵ cells/well; (ii) irradiated C57BL/6 splenocyte feeders (3,000 rads): 1×10⁶ cells/well; and (iii) 10 CU/ml IL-2.

Day 19: The bulk cultures (post two stimulations) were evaluated for specific reactivity via IFN-γ secretion upon co-culture with the tumor cell lines set forth in Table 3. Tumor cells were treated with IFNγ (20 ng/ml) and tumor necrosis factor alpha (3 ng/ml) overnight prior to the assay. The results are shown in Table 3 (IFN-γ (pg/ml)).

TABLE 3

| | HLA-A2 | NY-ESO-1 | RNA copies per GAPDH (×100) | Post 2 bulk stims. | | | |
|---|---|---|---|---|---|---|---|
| | | | | LPS blasts + 1 μg/ml peptide | T2 + 1 μg/ml peptide | T2 + 0.1 μg/ml peptide | T2 + 0.01 μg/ml peptide |
| T2 + HBV | + | − | nt | 195 | 2,860 | 16,156 | 1,058 |
| T2 + ESO: 157 | + | + | nt | 79,524 | 72,730 | 47,871 | 1,899 |
| media | − | − | nt | 137 | 131 | 156 | 406 |
| 888mel | − | − | 0.02 | 40 | 201 | 112 | 562 |
| Sk23mel | + | − | 0.01 | 79 | 245 | 562 | 424 |
| 1359mel | − | + | 5.68 | 73 | 169 | 188 | 357 |
| 1359-A2 | + | + | nt | 966 | 320 | 1,597 | 258 |
| A375mel | + | + | 59.08 | 150 | 176 | 258 | 332 |
| 624mel | + | + | 4.14 | 320 | 144 | 697 | 301 |
| 1390mel | + | + | nt | — | — | — | — |
| 1363mel | + | + | nt | — | — | — | — |
| COS-A2-CEA | + | − | nt | 226 | 369 | 400 | 308 |
| COS-A2-ESO | + | + | nt | 424 | 351 | 326 | 295 |
| 293-A2-gp100 | + | − | nt | — | — | — | — |
| 293-A2-ESO | + | + | nt | — | — | — | — |

Day 21: Bulk cultures were restimulated in 24-well plates under the following conditions: (i) irradiated T2 cells (18,000 rads) pulsed with 1, 0.1, or 0.01 μg/ml peptide: 5×10$^5$ cells/well; (ii) irradiated C57BL/6 splenocyte feeders (3,000 rads): 1×10$^6$ cells/well; and (iii) 10 CU/ml IL-2.

Day 30: The bulk cultures (post three stimulations) were evaluated for specific reactivity via IFN-γ secretion upon co-culture with the tumor cell lines set forth in Table 4. Tumor cells were treated with IFNγ (20 ng/ml) and tumor necrosis factor alpha (3 ng/ml) overnight prior to the assay. The results are shown in Table 4 (IFN-γ (pg/ml); * indicates bulk cultures that were cloned after three bulk stimulations).

TABLE 4

| | HLA-A2 | NY-ESO-1 | RNA copies per GAPDH (×100) | * LPS blasts + 1 μg/ml peptide | * T2 + 1 μg/ml peptide | T2 + 0.1 μg/ml peptide | T2 + 0.01 μg/ml peptide | TE8 (human T cell clone) |
|---|---|---|---|---|---|---|---|---|
| T2 + HBV | + | − | nt | 1,794 | 4,700 | 28,797 | 23,897 | 16 |
| T2 + ESO: 157 | + | + | nt | 78,316 | 63,793 | 96,164 | 19,698 | 16,254 |
| media | − | − | nt | 1,992 | 389 | 8,856 | 10,711 | 7 |
| 888mel | − | − | 0.02 | 1,268 | 188 | 6,611 | 7,614 | 13 |
| Sk23mel | + | − | 0.01 | 662 | 202 | 7,585 | 6,225 | 69 |
| 1359mel | − | + | 5.68 | 623 | 64 | 5,684 | 7,026 | 996 |
| 1359-A2 | + | + | nt | 27,572 | 7,774 | 10,324 | 7,204 | 7,936 |
| A375mel | + | + | 59.08 | 1,263 | 342 | 7,232 | 9,425 | 4,095 |
| 624mel | + | + | 4.14 | 14,098 | 3,211 | 10,061 | 8,727 | 3,262 |
| 1390mel | + | + | nt | 852 | 179 | 5,966 | 6,191 | 7,123 |
| 1363mel | + | + | nt | 42,970 | 15,673 | 20,398 | 9,958 | 12,149 |
| COS-A2-CEA | + | − | nt | 981 | 119 | 3,995 | 6,744 | 18 |
| COS-A2-ESO | + | + | nt | 19,523 | 3,334 | 9,116 | 8,187 | 14,662 |
| 293-A2-gp100 | + | − | nt | — | — | — | — | — |
| 293-A2-ESO | + | + | nt | — | — | — | — | — |

Day 33: Selected peptide/tumor reactive bulk cultures (post three stimulations) were cloned at 10 cells/well as described for Day 11 of Example 1.

Days 45-48: Growth positive wells were screened for peptide reactivity via IFN-γ secretion upon co-culture with the tumor cell lines set forth in Table 5. Tumor cells were treated with IFNγ (20 ng/ml) and tumor necrosis factor alpha (3 ng/ml) overnight prior to the assay.

The splenocytes stimulated with LPS-activated HLA-A2+ splenocytes (3,000 rads) pulsed with 1 μg/ml priming peptide and 10 μg/ml human β2-microgobulin on Day 0 produced 33 out of 960 growth positive wells. Data for the four most reactive clones (Nos. 2, 5, 6, and 8) are shown in Table 5 (post 3 bulk stimulations; IFN-γ (pg/ml)). The splenocytes stimulated with T2 cells (17,000 rads) pulsed with 1 μg/ml peptide produced 104 out of 960 growth positive wells. Data for the four most reactive clones (Nos. 1, 50, 51, and 63) are shown in Table 5.

TABLE 5

| | HLA-A2 | NY-ESO-1 | RNA copies per GAPDH (×100) | 2 | 5 | 6 |
|---|---|---|---|---|---|---|
| T2 + HBV | + | − | nt | 235 | 317 | 223 |
| T2 + ESO: 157 | + | + | nt | >14,000 | >14,000 | >14,000 |
| media | − | − | nt | 221 | 314 | 231 |
| 888mel | − | − | 0.02 | 210 | 316 | 208 |
| Sk23mel | + | − | 0.01 | 216 | 309 | 210 |
| 1359mel | − | + | 5.68 | 243 | 383 | 206 |
| 1359-A2 | + | + | nt | 1,981 | 6,027 | 2,523 |
| A375mel | + | + | 59.08 | 523 | 388 | 232 |
| 624mel | + | + | 4.14 | 7,879 | 1,931 | 2,527 |
| 1390mel | + | + | nt | 1,124 | 17,567 | 352 |
| 1363mel | + | + | nt | — | — | — |
| COS-A2-CEA | + | − | nt | — | — | — |
| COS-A2-ESO | + | + | nt | — | — | — |
| 293-A2-gp100 | + | − | nt | — | — | — |
| 293-A2-ESO | + | + | nt | — | — | — |

| | 8 | 1 | 50 | 51 | 63 |
|---|---|---|---|---|---|
| T2 + HBV | 344 | 306 | 335 | 270 | 239 |
| T2 + ESO: 157 | >14,000 | >14,000 | >14,000 | >14,000 | >14,000 |
| media | 563 | 266 | 232 | 258 | 222 |
| 888mel | 288 | 234 | 241 | 244 | 208 |
| Sk23mel | 297 | 278 | 208 | 222 | 207 |
| 1359mel | 422 | 347 | 271 | 212 | 229 |
| 1359-A2 | 1,845 | 1,477 | 3,661 | 1,965 | 2,272 |
| A375mel | 1,455 | 556 | 557 | 556 | 737 |
| 624mel | 8,595 | 4,629 | 4,487 | 2,978 | 7,139 |
| 1390mel | 900 | 517 | 379 | 914 | 716 |
| 1363mel | — | — | — | — | — |
| COS-A2-CEA | — | — | — | — | — |
| COS-A2-ESO | — | — | — | — | — |
| 293-A2-gp100 | — | — | — | — | — |
| 293-A2-ESO | — | — | — | — | — |

Days 46-49: Peptide reactive clones were restimulated in 24-well plates as described for Day 21 of this example. Restimulated clones were flash-frozen for RNA preparation.

Example 3

This example demonstrates the isolation of a murine anti-NY-ESO-1 TCR and the specific reactivity of the isolated TCR against NY-ESO-1.

The TCR from five clones, (namely, clones B, H, 5, 6, 1, 50, and 63) were isolated. The nucleotide sequence (RNA) encoding the TCR of each clone was isolated, sequenced, and transfected into human peripheral blood mononuclear cells (PBMC) from Patients 1 and 2. The transfected cells were stimulated with OKT3 and IL-2 and cultured alone (media) or co-cultured with T2 cells pulsed with control (HBV) peptide, T2 cells pulsed with NY-ESO-1$_{157-165}$ peptide, COA-A2-CEA (NY-ESO-1$^-$), COS-A2-ESO (NY-ESO-1$^+$), or one of various melanoma tumor cell lines 888mel (NY-ESO-1$^-$), Sk23mel (NY-ESO-1$^-$), A375mel (NY-ESO-1$^+$), 1363mel (NY-ESO-1$^+$), 1390 (NY-ESO-1$^+$), or 624 (NY-ESO-1$^+$). IFNγ secretion was measured. The results are shown in Table 6 (IFNγ (pg/ml)).

TABLE 6

| | T2 + HBV | T2 + ESO: 157 | media | 888 | Sk23 | 1363 | 1390 | A375 | 624 | COS-A2-CEA | COS-A2-ESO |
|---|---|---|---|---|---|---|---|---|---|---|---|
| HLA-A2 | − | − | − | − | + | + | + | + | + | + | + |
| NY-ESO-1 | − | + | − | − | − | + | + | + | + | − | + |
| *Patient 1* | | | | | | | | | | | |
| GFP | 326 | 180 | 8 | 198 | 134 | 220 | 325 | 632 | 32 | 94 | 74 |
| Avidex TCR | 235 | >10,000 | 7 | 188 | 81 | >10,000 | 1637 | 5752 | 531 | 52 | 2320 |
| TRAV7D-4/TRBV19[1] | 664 | >10,000 | 7 | 185 | 102 | 2262 | 489 | 893 | 39 | 72 | 449 |
| TRAV13D-2/TRBV14[2] | 197 | >10,000 | 8 | 152 | 88 | 134 | 159 | 338 | 26 | 75 | 55 |
| TRAV7D-3/TRBV14[3] | 155 | 366 | 7 | 129 | 112 | 122 | 171 | 378 | 28 | 68 | 71 |
| TRAV6D/TRBV26[4] | 198 | >10,000 | 11 | 255 | 156 | >10,000 | 3859 | 9973 | 782 | 91 | 3872 |
| TRAV7D-3/TRBV26[5] | 190 | 1269 | 0 | 208 | 107 | 246 | 189 | 509 | 34 | 79 | 104 |
| *Patient 2* | | | | | | | | | | | |
| GFP | 26 | 30 | 2 | 47 | 27 | 22 | 62 | 98 | 8 | 16 | 19 |
| Avidex TCR | 50 | >10,000 | 4 | 32 | 22 | 2484 | 208 | 192 | 150 | 11 | 588 |
| TRAV7D-4/TRBV19[1] | 183 | >10,000 | 2 | 34 | 15 | 149 | 47 | 39 | 7 | 13 | 90 |
| TRAV13D-2/TRBV14[2] | 22 | 7898 | 9 | 27 | 13 | 20 | 42 | 58 | 11 | 22 | 17 |
| TRAV7D-3/TRBV14[3] | 24 | 23 | 11 | 28 | 13 | 21 | 30 | 39 | 5 | 7 | 13 |
| TRAV6D/TRBV26[4] | 63 | >10,000 | 39 | 77 | 40 | 3597 | 777 | 344 | 133 | 32 | 683 |
| TRAV7D-3/TRBV26[5] | 10 | 77 | 0 | 28 | 17 | 27 | 33 | 51 | 5 | 16 | 40 |

[1]TRAV7D-4/TRBV19: Clone ESO (1 stim LPS) B (Table 2 above)
[2]TRAV13D-2/TRBV14: Clone ESO (1 stim LPS) H (Table 2 above)
[3]TRAV7D-3/TRBV14: Clone ESO (3 stim LPS) 5 (Table 5 above)
[4]TRAV6D/TRBV26: Clones ESO (3 stim LPS) 6; ESO (3 stim T2) 1; ESO (3 stim T2) 63 (Table 5 above)
[5]TRAV7D-3/TRBV26: Clone ESO (3 stim T2) 50 (Table 5 above)

As shown in Table 6, the TRAV6D/TRBV26 (SEQ ID NOs: 11 and 12) TCR provided the highest specific anti-NY-ESO-1 reactivity and was chosen for further study.

The nucleotide sequence (RNA) encoding the TRAV6D/TRBV26 (SEQ ID NOs: 11 and 12) TCR was transfected into human PBMC from Patients 3 and 4. The transfected cells were positively selected for CD8+ and CD4+ cells, stimulated with OKT3 and IL-2, and cultured alone (media) or co-cultured with T2 cells pulsed with control (HBV) peptide, T2 cells pulsed with various concentrations of NY-ESO-1$_{157-165}$ peptide, COS-A2-ESO (NY-ESO-1$^+$), COA-A2-CEA (NY-ESO-1$^-$), or one of various melanoma tumor cell lines 888mel (NY-ESO-1$^-$), Sk23mel (NY-ESO-1$^-$), A375mel (NY-ESO-1$^+$), 1363mel (NY-ESO-1$^+$), or 624 (NY-ESO-1$^+$). IFNγ secretion was measured and the results are shown in Table 7 (IFNγ (pg/ml)).

As shown in Table 7, the cells transfected with the TRAV6D/TRBV26 (SEQ ID NOs: 11 and 12) TCR specifically recognized NY-ESO-1+ melanoma tumor cells, as measured by IFNγ secretion.

Example 4

This example demonstrates the reactivity of human CD8+ and CD4+ T cells transfected with a murine anti-NY-ESO-1 TCR upon co-culture with dendritic cells pulsed with NY-ESO-1 peptide.

CD8+ (FIG. 1A) or CD4+ (FIG. 1B) human T cells were transfected with a murine anti-NY-ESO-1 TCR (TRAV6D/TRBV26 (SEQ ID NOs: 11 and 12)) or a human anti-NY-ESO-1 TCR. The transfected cells were co-cultured with

TABLE 7

| | | T2 + HBV 10$^{-6}$ g/ml | T2 + ESO: 157-165 | | | | | | | media |
|---|---|---|---|---|---|---|---|---|---|---|
| | | | 10$^{-12}$ g/ml | 10$^{-11}$ g/ml | 10$^{-10}$ g/ml | 10$^{-9}$ g/ml | 10$^{-8}$ g/ml | 10$^{-7}$ g/ml | 10$^{-6}$ g/ml | |
| | | | | | Patient 3 | | | | | |
| CD8+ | TRAV6D/TRBV26 | 243 | 238 | 1075 | 4257 | 6170 | 8996 | 5087 | 6142 | 122 |
| | GFP | 86 | 47 | 27 | 29 | 9 | 17 | 18 | 25 | 12 |
| CD4+ | TRAV6D/TRBV26 | 127 | 67 | 69 | 1836 | 12835 | 19161 | 12495 | 14641 | 173 |
| | Avidex | 6 | 0 | 1 | 40 | 1147 | 2455 | 3538 | 5783 | 17 |
| | GFP | 10 | 0 | 0 | 0 | 0 | 0 | 0 | 0 | 10 |
| | | | | | Patient 4 | | | | | |
| CD8+ | TRAV6D/TRBV26 | 15 | 55 | 931 | 1713 | 2670 | 3721 | 2988 | 2878 | 0 |
| | GFP | 42 | 0 | 0 | 0 | 0 | 0 | 5 | 0 | 0 |
| CD4+ | TRAV6D/TRBV26 | 38 | 1 | 58 | 5774 | 18051 | 19691 | >20000 | >20000 | 21 |
| | Avidex | 25 | 0 | 0 | 200 | 2923 | 15574 | >20000 | 18293 | 8 |
| | GFP | 12 | 0 | 0 | 0 | 0 | 0 | 10 | 30 | 0 |

| | | 888 A2− ESO− | Sk23 A2+ ESO− | A375 A2+ ESO+ | 624 A2+ ESO+ | 1363 A2+ ESO+ | COS-A2 CEA A2+ ESO− | COS-A2 ESO A2+ ESO+ |
|---|---|---|---|---|---|---|---|---|
| | | | | Patient 3 | | | | |
| CD8+ | TRAV6D/TRBV26 | 90 | 70 | 419 | 125 | 1194 | 56 | 1041 |
| | GFP | 19 | 5 | 18 | 1 | 27 | 11 | 20 |
| CD4+ | TRAV6D/TRBV26 | 56 | 43 | 250 | 84 | 361 | 30 | 179 |
| | Avidex | 0 | 0 | 25 | 9 | 26 | 10 | 14 |
| | GFP | 5 | 0 | 43 | 18 | 47 | 4 | 7 |
| | | | | Patient 4 | | | | |
| CD8+ | TRAV6D/TRBV26 | 0 | 0 | 48 | 15 | 262 | 0 | 380 |
| | GFP | 0 | 6 | 5 | 0 | 0 | 2 | 0 |
| CD4+ | TRAV6D/TRBV26 | 7 | 0 | 109 | 36 | 476 | 2 | 241 |
| | Avidex | 0 | 0 | 37 | 0 | 60 | 0 | 23 |
| | GFP | 0 | 0 | 28 | 14 | 42 | 0 | 0 | dendritic cells pulsed with various concentrations of NY-ESO-1$_{157-165}$ peptide, and IFNγ secretion was measured.

As shown in FIGS. 1A and 1B, CD8+ and CD4+ human T cells transfected with a murine anti-NY-ESO-1 TCR (TRAV6D/TRBV26 (SEQ ID NOs: 11 and 12)) were reactive against dendritic cells pulsed with NY-ESO-1$_{157-165}$ peptide, as measured by IFNγ secretion. CD8+ human T cells transfected with a murine anti-NY-ESO-1 TCR (TRAV6D/TRBV26 (SEQ ID NOs: 11 and 12)) were more reactive against dendritic cells pulsed with NY-ESO-1$_{157-165}$ peptide, as measured by IFNγ secretion, as compared to CD8+ cells transfected with a human anti-NY-ESO-1 TCR.

Example 5

This example demonstrates the reactivity of human CD8+ and CD4+ T cells transfected with a murine anti-NY-ESO-1 TCR upon co-culture with melanoma tumor cells.

CD8+ (FIG. 2A) or CD4+ (FIG. 2B) human T cells were transfected with a murine anti-NY-ESO-1 TCR (TRAV6D/TRBV26 (SEQ ID NOs: 11 and 12)) or a human anti-NY-ESO-1 TCR. The transfected cells were cultured alone (media) or co-cultured with T2 cells pulsed with control peptide, T2 cells pulsed with NY-ESO-1$_{157-165}$ peptide, COA-A2-CEA (NY-ESO-1−), COS-A2-ESO (NY-ESO-1+), or one of various melanoma tumor cell lines 888mel (NY-ESO-1−), Sk23mel (NY-ESO-1−), A375mel (NY-ESO-1+), or 1363mel (NY-ESO-1+). IFNγ secretion was measured.

Figure 2A:
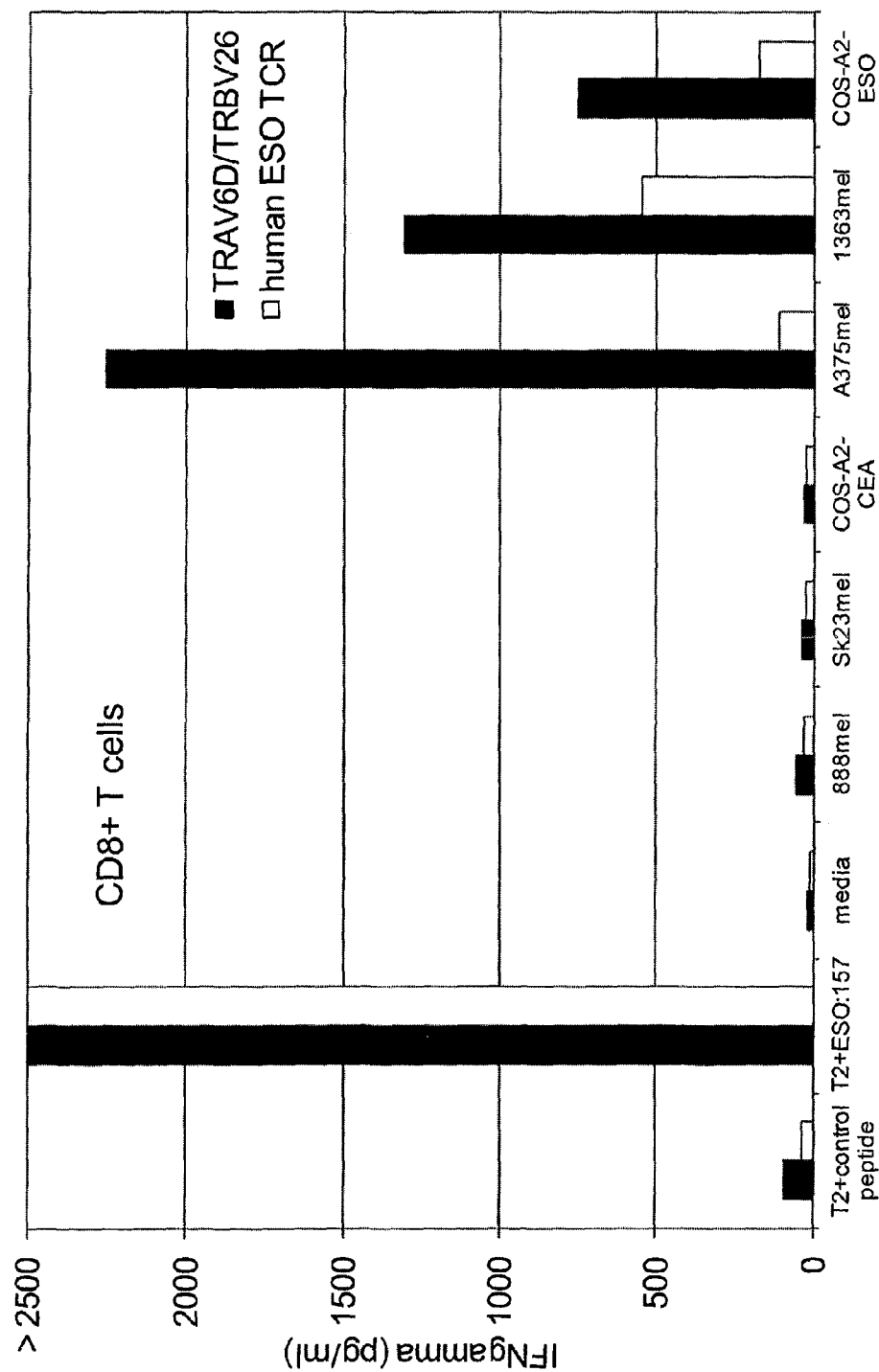
Figure 2B:
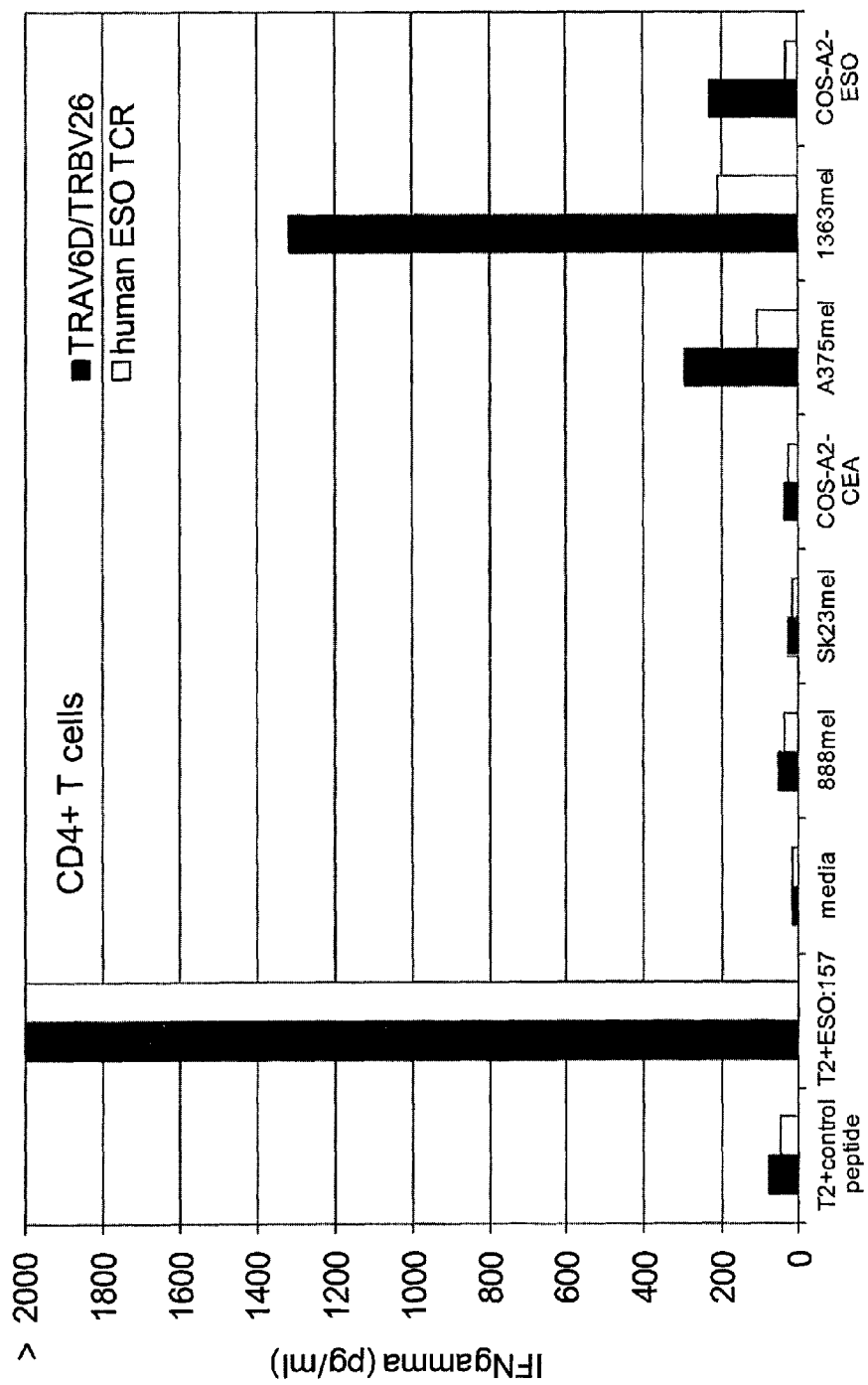

As shown in FIGS. 2A and 2B, CD8+ and CD4+ human T cells transfected with a murine anti-NY-ESO-1 TCR (TRAV6D/TRBV26 (SEQ ID NOs: 11 and 12)) specifically recognized NY-ESO-1+ melanoma tumor cells, as measured by IFNγ secretion. CD8+ and CD4+ human T cells transfected with a murine anti-NY-ESO-1 TCR (TRAV6D/TRBV26 (SEQ ID NOs: 11 and 12)) were more reactive against NY-ESO-1+ tumor cell lines, as measured by IFNγ secretion, as compared to CD8+ and CD4+ cells transfected with a human anti-NY-ESO-1 TCR.

Example 6

This example demonstrates the reactivity of human CD8+ and CD4+ T cells transfected with a wild-type or codon-optimized nucleotide sequence encoding a murine anti-NY-ESO-1 TCR upon co-culture with melanoma tumor cells.

A wild-type (SEQ ID NOs: 19 and 20) or codon-optimized (SEQ ID NOs: 15 and 16) nucleotide sequence (RNA) encoding the murine anti-NY-ESO-1 TCR (TRAV6D/TRBV26) was transfected into CD8+ or CD4+ human PBMC from Patients 5 and 6. The transfected cells were positively selected for CD8+ and CD4+ cells, stimulated with OKT3 and IL-2, and cultured alone (media) or co-cultured with T2 cells pulsed with control (HBVc) peptide, T2 cells pulsed with various concentrations of NY-ESO-1$_{157-165}$ peptide, COA-A2-CEA (NY-ESO-1−), COS-A2-ESO (NY-ESO-1+), or one of various melanoma tumor cell lines 888mel (NY-ESO-1−), Sk23mel (NY-ESO-1−), A375mel (NY-ESO-1+), 1363mel (NY-ESO-1+), A375 (NY-ESO-1+), or 624mel (NY-ESO-1+). IFNγ secretion was measured. The results are shown in Table 8 (IFNγ (pg/ml)).

TABLE 8

| | Patient 5 CD4 | | | Patient 5 CD8 | | | Patient 6 CD4 | | | Patient 6 CD8 | | | |
|---|---|---|---|---|---|---|---|---|---|---|---|---|---|
| | Codon optimized | wild type | GFP | Codon optimized | wild type | GFP | Codon optimized | wild type | GFP | Codon optimized | wild type | GFP | media |
| media | 103 | 62 | 6 | 43 | 60 | 1 | 0 | 0 | 0 | 0 | 0 | 0 | 3 |
| T2 + HBVc | 58 | 37 | 4 | 71 | 108 | 82 | 2 | 17 | 7 | 3 | 12 | 9 | 8 |
| T2 + 10$^{-12}$ M ESO | 44 | 32 | 0 | 67 | 86 | 46 | 13 | 15 | 6 | 6 | 9 | 14 | 0 |
| T2 + 10$^{-11}$ M ESO | 83 | 42 | 0 | 52 | 150 | 30 | 15 | 22 | 7 | 20 | 23 | 2 | 0 |
| T2 + 10$^{-10}$ M ESO | 69 | 27 | 3 | 221 | 175 | 43 | 13 | 18 | 4 | 193 | 176 | 0 | 0 |
| T2 + 10$^{-9}$ M ESO | 232 | 60 | 0 | 3149 | 2465 | 20 | 728 | 555 | 6 | 1979 | 3066 | 4 | 0 |
| T2 + 10$^{-8}$ M ESO | 5158 | 2979 | 0 | 13308 | 13394 | 56 | 15468 | 12906 | 7 | 5382 | 11217 | 0 | 0 |
| T2 + 10$^{-7}$ M ESO | 13987 | 9362 | 1 | >20000 | >20000 | 37 | 23981 | 21321 | 8 | 8914 | 13127 | 0 | 0 |
| T2 + 10$^{-6}$ M ESO | 15345 | 9417 | 0 | >20000 | >20000 | 51 | 26802 | 25225 | 8 | 14734 | 19766 | 2 | 0 |
| 888mel (A2− ESO−) | 54 | 30 | 8 | 55 | 98 | 37 | 22 | 9 | 8 | 36 | 58 | 37 | 17 |
| Sk23mel (A2+ ESO−) | 30 | 34 | 7 | 8 | 26 | 29 | 3 | 0 | 3 | 8 | 29 | 11 | 0 |
| A375 (A2+ ESO+) | 239 | 204 | 75 | 525 | 925 | 55 | 114 | 146 | 82 | 190 | 480 | 22 | 0 |
| 624mel (A2+ ESO+) | 102 | 81 | 57 | 176 | 211 | 24 | 44 | 42 | 6 | 89 | 125 | 0 | 0 |
| 1363mel (A2+ ESO+) | 605 | 443 | 176 | 964 | 1421 | 28 | 525 | 576 | 153 | 426 | 1079 | 20 | nt |
| COS-A2-CEA | 68 | 66 | 22 | 51 | 83 | 39 | 8 | 17 | 16 | 4 | 13 | 9 | 4 |
| COS-A2-ESO | 429 | 92 | 2 | 1322 | 1436 | 22 | 1213 | 431 | 17 | 872 | 1372 | 10 | 0 |

As shown in Table 8, CD8+ and CD4+ human T cells transfected with a wild-type or codon-optimized nucleotide sequence encoding a murine anti-NY-ESO-1 TCR (TRAV6D/TRBV26) specifically recognized NY-ESO-1+ melanoma tumor cells, as measured by IFNγ secretion.

Example 7

This example demonstrates the reactivity of human CD8+ T cells transfected with a wild-type nucleotide sequence encoding a murine anti-NY-ESO-1 TCR upon co-culture with melanoma and non-melanoma tumor cells.

A nucleotide sequence (RNA) (SEQ ID NO: 19 and 20) encoding the murine anti-NY-ESO-1 TCR (TRAV6D/TRBV26) was electroporated into CD8+ human T cells from Patients 7 and 8. Untransfected cells (mock) or transfected cells were positively selected for CD8+ T cells, stimulated with OKT3 and IL-2, and cultured alone (media) or co-cultured with T2 cells pulsed with control (HBVc) peptide; T2 cells pulsed with various concentrations of NY-ESO-$1_{157-165}$ peptide; COA-A2-CEA (NY-ESO-1$^-$); COS-A2-ESO (NY-ESO-1$^+$); one of various melanoma tumor cell lines 888mel (NY-ESO-1$^-$), Sk23mel (NY-ESO-1$^-$), A375mel (NY-ESO-1$^+$), 1363mel (NY-ESO-1$^+$), A375 (NY-ESO-1$^+$); osteogenic sarcoma cell line Saos2 (NY-ESO-1$^+$); glioma cell line LN-18 (NY-ESO-1$^+$); Ewing's sarcoma cell line TC-71 (NY-ESO-1$^+$); neuroblastoma cell lines SKN AS (NY-ESO-1$^+$) or SKN AS-A2 (NY-ESO-1$^+$); or breast cancer cell lines MDA 453S (NY-ESO-1$^+$) or MDA 453S-A2 (NY-ESO-1$^+$). IFNγ secretion was measured. The results are shown in Table 9 (IFNγ (pg/ml)).

Example 8

This example demonstrates the preparation of recombinant expression vectors encoding a murine anti-NY-ESO-1 TCR.

A retroviral vector comprising DNA encoding wild-type human anti-NY-ESO-1 TCR (1G4), 1G4 TCR having a double substitution within the CDR3α chain in which leucine and tyrosine are substituted for threonine at position 95 (1G4-LY) (Robbins et al., *J. Clin. Oncol.*, 29: 917-924 (2011); Robbins et al., *J. Immunol.*, 180: 6116-6131 (2008)), or murine anti-NY-ESO-1 TCR (TRAV6D/TRBV26) (SEQ ID NOs: 11 and 12) were cloned into a MSGV1 retroviral backbone and transformed into TOP10 cells. A picornavirus 2A peptide (SEQ ID NO: 13) linked the alpha and beta chains. Two vectors encoding the murine TRAV6D/TRBV26 TCR were made: one contained the nucleotide sequence encoding the alpha chain located 5' of the nucleotide sequence encoding the beta chain (mESOαβ) (SEQ ID NO: 17), and one contained the nucleotide sequence encoding the beta chain located 5' of the nucleotide sequence encoding the alpha chain (mESOβα) (SEQ ID NO: 18). The presence of the inserts encoding the alpha and beta chains of the TCR was confirmed by digestion with Nco I and Not I restriction enzymes. DNA was generated from one clone for each of the human and murine TCRs by maxiprep.

DNA from the 1G4 TCR and 1G4-LY vectors was transfected into 293GP cells to collect supernatant and transduce PBL in subsequent transduction experiments. A vector encoding GFP was used as a control.

TABLE 9

| | | Patient 7 CD8 | | Patient 8 CD8 | | |
|---|---|---|---|---|---|---|
| | | ESO a/b | mock | ESO a/b | mock | media |
| media | | 21 | 0 | 0 | 6 | 0 |
| T2 + HBVc | | 64 | 60 | 88 | 50 | 0 |
| T2 + 10 – 12 M ESO | | 50 | 58 | 107 | 59 | 0 |
| T2 + 10 – 11 M ESO | | 66 | 51 | 209 | 71 | 0 |
| T2 + 10 – 10 M ESO | | 332 | 66 | 1704 | 50 | 0 |
| T2 + 10 – 9 M ESO | | 3142 | 51 | 10886 | 55 | 0 |
| T2 + 10 – 8 M ESO | | 6505 | 52 | >20000 | 58 | 0 |
| T2 + 10 – 7 M ESO | | 6764 | 42 | >20000 | 51 | 0 |
| T2 + 10 – 6 M ESO | | 6550 | 55 | >20000 | 58 | 0 |
| 888mel (A2– ESO–) | melanoma | 59 | 45 | 142 | 133 | 0 |
| Sk23mel (A2+ ESO–) | melanoma | 79 | 54 | 31 | 59 | 0 |
| A375mel (A2+ ESO+) | melanoma | 2986 | 240 | 1984 | 93 | 0 |
| 1363mel (A2+ ESO+) | melanoma | 1889 | 119 | 9858 | 137 | 0 |
| Saos2 (A2+ ESO+) | osteogenic sarcoma | 248 | 34 | 1253 | 28 | 0 |
| LN-18 (A2+ ESO+) | glioma | 123 | 21 | 224 | 34 | 0 |
| TC-71 (A2+ ESO+) | Ewing's sarcoma | 159 | 116 | 183 | 127 | 3 |
| SKN AS (A2– ESO+) | neuroblastoma | 542 | 328 | 199 | 207 | 2 |
| SKN AS - A2 (A2+ ESO+) | neuroblastoma | 148 | 38 | 1004 | 39 | 0 |
| MDA 453S (A2– ESO+) | breast cancer | 448 | 311 | 177 | 230 | 0 |
| MDA 453S -A2 (A2+ ESO+) | breast cancer | 111 | 50 | 610 | 39 | 0 |
| COS-A2–CEA (A2+ ESO–) | | 45 | 51 | 50 | 63 | 7 |
| COS-A2–ESO (A2+ ESO+) | | 588 | 34 | 4109 | 63 | 0 |

As shown in Table 9, CD8+ human T cells transfected with a nucleotide sequence encoding a murine anti-NY-ESO-1 TCR (TRAV6D/TRBV26) specifically recognized NY-ESO-1+ melanoma, osteogenic sarcoma, Ewing's sarcoma, neuroblastoma, and breast cancer tumor cells, as measured by IFNγ secretion.

Example 9

This example demonstrates the transduction efficiency of a murine anti-NY-ESO-1 TCR.

Peripheral blood lymphocytes (PBL) were stimulated with OKT3 on Day 0 (S1). The PBL were transduced with the 1G4, 1G4-LY, mESOαβ, or mESOβα TCR vector of Example 8 on Days 3 and 4. On Days 7-11, transduction efficiency was evaluated by fluorescence-activated cell sorting (FACS). An antibody recognizing the variable region of the murine TCR (VB13.1) and an antibody recognizing the constant region of the murine TCR (mB) were used for the FACS. The FACS was performed 7 to 11 days after first stimulation (S1D7-S1D11). The results are summarized in Table 10 below.

TABLE 10

| | % VB13.1, mB+ cells pre-rapid expansion (REP) (for 5 donors) (S1D7-S1D11) |
|---|---|
| Untransduced (UT) | 0-6 |
| Green fluorescent protein (GFP) | 67-90.5 |
| 1G4 TCR | 62-85 |
| 1G4-LY TCR | 37-85 |
| mESOαβ TCR | 56-90 |
| mESOβα TCR | 56-91 |

As shown in Table 10, PBL transduced with the mESOαβ or mESOβα TCR vector were transduced with similar efficiency as compared to the vectors encoding the 1G4 and 1G4-LY TCRs.

Example 10

This example demonstrates the reactivity of cells transduced with a vector encoding a murine anti-NY-ESO-1 TCR.

PBL from five donors were stimulated and either untransduced or transduced with vectors encoding GFP or the 1G4-LY, mESOαβ, or mESOβα TCR as described in Example 9. Transduced PBL were co-cultured with one of the various tumor cell lines listed in Table 11A or 11B below or with T2 cells pulsed with SSX peptide, no peptide (T2), or one of the various concentrations of NY-ESO-1$_{157-165}$ peptide listed in Table 12 below. IFNγ secretion was measured by enzyme-linked immunosorbent assay (ELISA) of 24 hour supernatant from co-cultures. ELISA was performed 6, 7, or 10 days following first stimulation (S1D6, S1D7, and S1D10). The results are shown in Tables 11A, 11B, and 12 (IFNγ pg/ml). Transduction (Td) efficiency was based on FACS analysis of Vβ13.1+mβ+cells.

TABLE 11A

| | % td efficiency | 888 | 938 | COS-A2-gp100 | 624.38 | H1299-A2 | A375 | COAS-A2-ESO | 1300 |
|---|---|---|---|---|---|---|---|---|---|
| Patient 1 (Dilution 1:10; S1D7) | | | | | | | | | |
| Untransduced (UT) | N/A | 12 | 0 | 99 | 22 | 17 | 132 | 24 | 61 |
| GFP | 90 | 0 | 0 | 91 | 17 | 65 | 95 | 0 | 33 |
| 1G4-LY TCR | 85 | 13 | 0 | 99 | 3316 | 8592 | 3059 | 1391 | 5732 |
| mESOαβ TCR | 83 | 239 | 284 | 156 | 5523 | 9616 | 4430 | 1872 | 6922 |
| mESOβα TCR | 83 | 329 | 326 | 42 | 6721 | 9898 | 4178 | 2270 | 7798 |
| Patient 2 (Dilution 1:5; S1D7) | | | | | | | | | |
| Untransduced (UT) | N/A | 44 | 43 | 46 | 44 | 42 | 53 | 46 | 42 |
| GFP | 67 | 42 | 42 | 43 | 44 | 40 | 50 | 41 | 41 |
| 1G4-LY TCR | 63 | 53 | 43 | 44 | 346 | 1446 | 451 | 132 | 352 |
| mESOαβ TCR | 56 | 43 | 44 | 45 | 372 | 1259 | 415 | 108 | 323 |
| mESOβα TCR | 56 | 43 | 46 | 45 | 327 | 1236 | 412 | 136 | 625 |
| Patient 3 (Dilution 1:5; S1D10) | | | | | | | | | |
| Untransduced (UT) | N/A | 0 | 0 | 0 | 0 | 0 | 48 | 39 | — |
| GFP | 63 | 0 | 0 | 0 | 0 | 0 | 0 | 0 | — |
| 1G4-LY TCR | 76 | 0 | 305 | 0 | 546 | 770 | 1020 | 332 | — |
| mESOαβ TCR | 63 | 0 | 0 | 0 | 111 | 38 | 292 | 13 | — |
| mESOβα TCR | 60 | 0 | 0 | 0 | 413 | 540 | 819 | 283 | — |

TABLE 11B

| | % Td efficiency | Media | 888 | 938 | COS-A2 gp100 | 624.38 | H1299-A2 | A375 | COS-A2-ESO |
|---|---|---|---|---|---|---|---|---|---|
| Patient 4 (Dilution 1:5; S1D6) | | | | | | | | | |
| Untransduced (UT) | NA | 52 | 155 | 35 | 294 | 195 | 122 | 476 | 212 |
| GFP | 91% | 34 | 91 | 22 | 78 | 106 | 62 | 306 | 50 |
| 1G4-LY TCR | 75% | 86 | 113 | 54 | 313 | 2172 | 7187 | 1671 | 2394 |
| mESOαβ TCR | 84% | 41 | 131 | 98 | 185 | 1946 | 5744 | 1064 | 1490 |
| mESOβα TCR | 85% | 52 | 130 | 110 | 164 | 2812 | 7163 | 1262 | 1676 |
| Patient 5 (Dilution 1:5; S1D6) | | | | | | | | | |
| Untransduced (UT) | NA | 42 | 23 | 12 | 88 | 9 | 8 | 107 | 64 |
| GFP | 87% | 15 | 20 | 15 | 76 | 0 | 11 | 98 | 62 |
| 1G4-LY TCR | 25% | 63 | 16 | 10 | 20 | 1172 | 3156 | 918 | 430 |

TABLE 11B-continued

| | % Td efficiency | Media | 888 | 938 | COS-A2 gp100 | 624.38 | H1299-A2 | A375 | COS-A2-ESO |
|---|---|---|---|---|---|---|---|---|---|
| mESOαβ TCR | 74% | 19 | 55 | 22 | 57 | <u>444</u> | <u>917</u> | <u>233</u> | <u>372</u> |
| mESOβα TCR | 74% | 15 | 32 | 20 | 24 | <u>810</u> | <u>2417</u> | <u>603</u> | <u>380</u> |

TABLE 12

| | % td efficiency | SSX | T2 | 1 µg/ml | 100 ng/ml | 10 ng/ml | 1 ng/ml | 0.1 ng/ml |
|---|---|---|---|---|---|---|---|---|
| Patient 1 (Dilution 1:5; S1D7) | | | | | | | | |
| Untransduced (UT) | NA | 0 | 0 | 0 | 0 | 0 | 0 | 0 |
| GFP | 90 | 0 | 0 | 0 | 0 | 0 | 0 | 0 |
| 1G4 TCR | 85 | 0 | 0 | <u>2452</u> | <u>2475</u> | <u>1525</u> | <u>851</u> | 99 |
| 1G4-LY TCR | 85 | 0 | 0 | <u>2173</u> | <u>1599</u> | <u>1087</u> | <u>677</u> | 0 |
| mESOαβ TCR | 83 | 0 | 0 | <u>2825</u> | <u>2210</u> | <u>1904</u> | <u>1060</u> | <u>278</u> |
| mESOβα TCR | 83 | 0 | 0 | <u>3018</u> | <u>2403</u> | <u>2020</u> | <u>1212</u> | <u>522</u> |
| Patient 2 (Dilution 1:5; S1D7) | | | | | | | | |
| Untransduced (UT) | NA | 22 | 20 | 52 | 24 | 21 | 33 | 53 |
| GFP | 67 | 17 | 38 | 33 | 39 | 31 | 21 | 20 |
| 1G4 TCR | 62 | 19 | 15 | 1,963 | 1,104 | 860 | <u>397</u> | 41 |
| 1G4-LY TCR | 63 | 15 | 19 | <u>2441</u> | <u>1280</u> | <u>879</u> | <u>291</u> | 40 |
| mESOαβ TCR | 56 | 20 | 42 | <u>4645</u> | <u>1854</u> | <u>1529</u> | <u>535</u> | 92 |
| mESOβα TCR | 56 | 38 | 27 | <u>7091</u> | <u>2302</u> | <u>1336</u> | <u>348</u> | <u>262</u> |

Cells transduced with the mESOαβ or the mESOβα TCR vectors specifically recognized NY-ESO-1$^+$/HLA-A*0201$^+$ target tumor cell lines but not HLA-A*0201$^-$NY-ESO-1$^+$ or HLA-A*0201$^+$/NY-ESO-1$^-$ cell lines as measured by IFNγ secretion (Tables 11A and 11B). Cells transduced with the mESOαβ or the mESOβα TCR vectors specifically recognized T2 cells pulsed with NY-ESO-1 peptide as measured by IFNγ secretion (Table 12). The NY-ESO-1 specific recognition was consistent among cells from five different donors. Functionality of the cells transduced with the murine anti-NY-ESO-1 TCR was comparable to that of cells transduced with human anti-NY-ESO-1 TCR. Functionality of the cells transduced with the mESβα TCR vector was slightly higher as compared to that of the cells transduced with the mESαβ TCR vector. PBL transduced with either mESOαβ or the mESOβα TCR vectors recognized T2 cells pulsed with as little as 1 ng/mL, indicating that both mTCRs are relatively high avidity receptors. Co-culture of PBL expressing mESOαβ or the mESOβα TCR vectors with control T2 cells that were not pulsed with any peptide produced background levels of IFN-γ. The cells of Patient 1 transduced with mESOβα TCR had higher levels of IFN-γ secretion when compared to the cells transduced with mESOαβ TCR for the same level of peptide. The cells of Patient 2 transduced with mESOβα TCR had higher levels of IFN-γ secretion when compared to the cells transduced with mESOαβ TCR for the same level of peptide for peptide concentrations 1 µg/ml, 100 ng/ml, and 0.1 ng/ml.

Example 11

This example demonstrates that cells transduced with a vector encoding a murine anti-NY-ESO-1 TCR maintain expression of the murine anti-NY-ESO-1 TCR following expansion of the numbers of cells.

PBL from two donors were stimulated and either untransduced or transduced with vectors encoding GFP or the 1G4, 1G4-LY, mESOαβ, or mESOβα TCR as described in Example 9. The numbers of PBL were expanded as described in Riddell et al., *Science,* 257:238-241 (1992) and Dudley et al., *Cancer J. Sci. Am.,* 6:69-77 (2000). Generally, the numbers of PBL were expanded up to 3 logs using soluble OKT3, irradiated feeder cells, and high-dose IL-2. Expression of murine anti-NY-ESO-1 TCR by expanded numbers (expanded once) of cells was measured by FACS twice (on Days 10 and 20). The results are summarized in Table 13 (% VB13.1, mB+ cells following expansion).

TABLE 13

| | Donor | | | |
|---|---|---|---|---|
| | 1 | | 2 | |
| | D10 | D20 | D10 | D20 |
| UT | 0 | <1 | 0 | <1 |
| GFP | 88 | 87 | 42 | 70 |
| 1G4 TCR | 59 | 80 | 50 | 59 |
| 1G4-LY TCR | 76 | 88 | 37 | 60 |
| mESOαβ TCR | 82 | 76 | 62 | 46 |
| mESOβα TCR | 82 | 74 | 62 | 50 |

As shown in Table 13, PBL transduced with the mESOαβ or mESOβα TCR vector maintained expression of the murine anti-NY-ESO-1 TCR following expansion of the numbers of cells.

Example 12

This example demonstrates that cells transduced with a vector encoding a murine anti-NY-ESO-1 TCR maintain functionality following expansion of the numbers of transduced cells.

PBL from two donors were stimulated and either untransduced or transduced with vectors encoding GFP or the 1G4-LY, mESOαβ, or mESOβα TCR as described in Example 9. The numbers of transduced cells were expanded as described in Example 11. Transduced expanded PBL were cultured alone (media) or co-cultured with one of the various tumor cell lines listed in Table 14 below or with T2 cells pulsed with SSX peptide, no peptide (T2), or one of the various concentrations of NY-ESO-1$_{157-165}$ peptide listed in Table 15 below. IFNγ secretion was measured by ELISA nine days after the second stimulation (S2D9). The results are shown in Tables 14 and 15 (IFNγ pg/ml; Dilution 1:10).

TABLE 14

| | % td efficiency | Media | 888 | 938 | COS-A2-gp100 | 624.38 | H1299-A2 | A375 | COAS-A2-ESO | 1300 |
|---|---|---|---|---|---|---|---|---|---|---|
| Patient 1 | | | | | | | | | | |
| Untransduced (UT) | N/A | 282 | 181 | 91 | 515 | 78 | 128 | 779 | — | 91 |
| GFP | 88 | 95 | 87 | 44 | 216 | 44 | 48 | 783 | — | 53 |
| 1G4-LY TCR | 76 | 208 | 184 | 105 | 260 | 8233 | 12848 | 6454 | — | 2786 |
| mESOαβ TCR | 82 | 129 | 183 | 111 | 121 | 8132 | 11976 | 6152 | — | 3035 |
| mESOβα TCR | 82 | 92 | 194 | 130 | 148 | 9104 | 11381 | 6226 | — | 2654 |
| Patient 2 | | | | | | | | | | |
| (UT) | N/A | 297 | 276 | 195 | 231 | 151 | 144 | 353 | — | 167 |
| GFP37 | 42 | 393 | 380 | 205 | 272 | 146 | 186 | 465 | — | 168 |
| 1G4-LY TCR | 37 | 102 | 174 | 53 | 133 | 4571 | 5984 | 2420 | — | 2066 |
| mESOαβ TCR | 62 | 125 | 397 | 362 | 170 | 7382 | 9590 | 4681 | — | 3439 |
| mESOβα TCR | 62 | 137 | 323 | 370 | 130 | 6345 | 8250 | 4236 | — | 3054 |

TABLE 15

| | % td efficiency | SSX | T2 | 1 µg/ml | 100 ng/ml | 10 ng/ml | 1 ng/ml | 0.1 ng/ml |
|---|---|---|---|---|---|---|---|---|
| Patient 1 | | | | | | | | |
| Untransduced (UT) | NA | 365 | 479 | 123 | 113 | 168 | 168 | 231 |
| GFP | 88 | 0 | 30 | 0 | 0 | 0 | 0 | 0 |
| 1G4 TCR | 59 | 179 | 275 | 26446 | 19424 | 13530 | 6988 | 1277 |
| 1G4-LY TCR | 76 | 185 | 217 | 30639 | 21553 | 16246 | 7261 | 1328 |
| mESOαβ TCR | 82 | 511 | 516 | 26427 | 22062 | 16950 | 8601 | 1873 |
| mESOβα TCR | 82 | 399 | 384 | 27813 | 23052 | 16872 | 8076 | 2174 |
| Patient 2 | | | | | | | | |
| Untransduced (UT) | NA | 976 | 1281 | 886 | 616 | 680 | 782 | 764 |
| GFP | 42 | 660 | 912 | 505 | 697 | 726 | 591 | 763 |
| 1G4 TCR | 50 | 279 | 364 | 19505 | 12698 | 7350 | 3553 | 747 |
| 1G4-LY TCR | 37 | 150 | 110 | 19416 | 10632 | 6799 | 2495 | 662 |
| mESOαβ TCR | 62 | 386 | 460 | 19960 | 13887 | 9970 | 4488 | 1025 |
| mESOβα TCR | 62 | 379 | 611 | 16434 | 12708 | 9646 | 5266 | 1177 |

Functionality of expanded transduced cells was also evaluated by chromium release assay. Expanded transduced cells (effector cells) were co-cultured with target melanoma cells 624.38 cells (Table 16A) or A375 cells (Table 16B) at various effector:target (E:T) cell ratios, and the percentage of target cells lysed was measured. The results are shown in Tables 16A and 16B (percentage of target cells lysed).

TABLE 16A

| E:T Ratio | 1G4-LY TCR | mESOα/β TCR | mESOβ/α TCR | GFP |
|---|---|---|---|---|
| 40:1 | 71.0 | 69.0 | 68 | 20.0 |
| 13:1 | 59.0 | 64.0 | 62 | 13.0 |
| 4:1 | 54.0 | 73.0 | 46 | 23.0 |
| 1.5:1 | 42.0 | 40.0 | 39 | 2.0 |

TABLE 16B

| E:T Ratio | IG4-LY TCR | mESO α/β | mESO β/α | GFP |
|---|---|---|---|---|
| 40:1 | 43.0 | 49.0 | 51 | 21.0 |
| 13:1 | 43.0 | 47.0 | 50 | 16.0 |
| 4:1 | 36.0 | 28.0 | 32 | 8.0 |
| 1.5:1 | 29.0 | 31.0 | 32 | 6.0 |

As shown in Tables 14, 15, 16A, and 16B, cells transduced with a vector encoding a murine anti-NY-ESO-1 TCR maintained functionality following expansion of the numbers of transduced cells.

Example 13

This example demonstrates a method of producing packaging cell clones for the production of mESOβα TCR for potential clinical application.

DNA for the mESOβα TCR vector was used to produce retroviral vector packaging cell clones under conditions required for potential clinical application. Supernatant from six PG13 producer cell clones was used to transduce PBL. FACS analysis of transduced PBL using the anti-mouse TCR-β chain antibody revealed that each clone produced virus that mediated positive TCR transduction (Table 17). To assess the specific recognition of tumor cells, the mTCR engineered PBL from each PG13 producer cell clone were co-cultured with a panel of HLA-A*0201+ and HLA-A*0201− melanoma and lung tumor derived cell lines (Table 17). IFN-gamma was measured by ELISA. A comparison of the six mTCR PG13 producer clones showed that T cells transduced with Clone C1 released high levels of IFN-γ in response to HLA-A*0201+/NY-ESO-1+ tumor cell target H1299-A2 and demonstrated the highest transduction efficiency (Table 17). These responses were specific as background levels of IFN-γ were released in response to NY-ESO-1+/HLA-A*0201− cell lines and NY-ESO-1−/

HLA-A*0201⁺ cell lines by each clone (FIG. 2). Based on this analysis, Clone C1 was selected for the production of a master cell bank for subsequent production of good manufacturing practice (GMP) retroviral supernatant.

TABLE 17

| Clone | % mTCRβ | IFN-γ pg/ml | | | | |
|---|---|---|---|---|---|---|
| | | media | 888 | H1299A2 | 624.38 | A375 |
| UT | 4 | 122 | 1 | 0 | 0 | 146 |
| B2 | 30 | 39 | 46 | 2923 | 670 | 382 |
| C1 | 63 | 0 | 0 | 7529 | 942 | 257 |
| C12 | 42 | 10 | 0 | 3332 | 661 | 351 |
| D8 | 36 | 64 | 90 | 5773 | 675 | 439 |
| F2 | 47 | 31 | 38 | 5533 | 579 | 488 |
| H4 | 44 | 34 | 38 | 7185 | 531 | 459 |

Example 14

This example demonstrates the transduction efficiency of cells transduced with a mESOβα TCR using a retroviral supernatant from the packaging cell clone of Example 13.

To compare the respective NY-ESO-1 TCRs (murine, or mTCR, versus human, or hTCR (1G4-LY TCR)), FACS analysis of PBL transduced with retroviral supernatant from packaging cell clones using the anti-mouse TCR-Vβ chain and the anti-Vβ13.1 antibodies was performed after one stimulation with OKT3 and following a second large-scale expansion using the rapid expansion protocol (REP) (Table 18). Results demonstrated that both the mTCR and the hTCR had equivalent percentages of transduction after stimulation, with the mTCR having equal to or greater levels of transduction after REP (Table 18).

TABLE 18

| | % TCR | | | |
|---|---|---|---|---|
| | Donor H | | Donor E | |
| | After one stimulation with OKT3 | After expanding numbers of cells twice | After one stimulation with OKT3 | After expanding numbers of cells twice |
| UT | 4 | 13 | 4 | 8 |
| 1G4-LY TCR | 52 | 56 | 48 | 44 |
| mESOβα TCR | 56 | 61 | 46 | 66 |

Example 15

This example demonstrates the reactivity of cells transduced with a mESOβα TCR using a retroviral supernatant from the packaging cell clone of Example 13.

The recognition of each TCR was evaluated by subjecting the mTCR and the hTCR transduced T cells to co-culture with NY-ESO-1 peptide-pulsed T2 cells. Both the mTCR and the hTCR specifically secreted IFN-γ upon encounter with the antigenic peptide in a dose-dependent manner after one stimulation with OKT3 and after REP (Table 19). After one stimulation, both the mTCR and the hTCR recognized T2 cells pulsed with as little as 0.1 ng/mL indicating that both mTCRs are relatively high avidity receptors. Following the expansion of the numbers of cells, the mTCR released higher levels of IFN-γ compared to the hTCR vector transduced T cells at each concentration of peptide (Table 19). Co-culture of PBL expressing NY-ESO-1 mTCR or NY-ESO-1 hTCR with control T2 cells that were not pulsed with any peptide produced background levels of IFN-γ.

TABLE 19

| peptide concentration | T2 cells without peptide | 0.1 ng/μl | 1 ng/μl | 10 ng/μl | 100 ng/μl |
|---|---|---|---|---|---|
| | IFN-γ pg/ml | | | | |
| | Donor H (after stimulation with OKT3) | | | | |
| UT | 400 | 380 | 329 | 350 | 285 |
| GFP | 633 | 455 | 424 | 410 | 412 |
| 1G4-LY TCR | 1259 | 1400 | 1710 | 3016 | 3775 |
| mESOβα TCR | 1070 | 1316 | 1660 | 3091 | 3744 |
| | IFN-γ pg/ml | | | | |
| | Donor H (after expanding numbers of cells) | | | | |
| UT | 34 | 47 | 57 | 22 | 28 |
| GFP | 34 | 47 | 57 | 22 | 28 |
| 1G4-LY TCR | 24 | 89 | 512 | 2974 | 4341 |
| mESOβα TCR | 174 | 229 | 1456 | 6633 | 10683 |

To assess the specific recognition of tumor cells, the mTCR engineered PBL were co-cultured with a panel of HLA-A*0201⁺ and HLA-A*0201⁻ melanoma and lung tumor derived cell lines. Specific release of IFN-γ was observed when both the mTCR engineered PBL and the hTCR were co-cultured with HLA-A*0201⁺/NY-ESO-1⁺ cell lines but not HLA-A*0201⁻/NY-ESO-1⁺ or HLA-A*0201⁺/NY-ESO-1⁻ cell lines (Table 20 (representative experiments shown)).

TABLE 20

| | H1299-A2 | 624.38 | 1300 | 938 |
|---|---|---|---|---|
| | Patient H | | | |
| Untransduced (UT) | 86 | 93 | 118 | 0 |
| GFP | 83 | 81 | 91 | 0 |
| 1G4-LY TCR | 14549 | 6171 | 1507 | 0 |
| mESOβα TCR | 8877 | 4248 | 1326 | 0 |
| | Patient E | | | |
| Untransduced (UT) | 64 | 72 | 81 | 0 |
| GFP | 70 | 72 | 63 | 0 |
| 1G4-LY TCR | 7483 | 2149 | 452 | 0 |
| mESOβα TCR | 10646 | 3548 | 986 | 0 |

Example 16

This example demonstrates specific lysis of melanoma cells by cells transduced with a mESOβα TCR using a retroviral supernatant from the packaging cell clone of Example 13.

The specific lysis of melanoma cell lines by the mTCR and the hTCR were also compared. The ability of the transduced PBL to lyse HLA-A*0201⁺/NY-ESO-1⁺ tumor cells was measured using a CYTOTOX-GLO biolumines- cence assay (Promega, Madison, Wis.). This assay utilizes a luminogenic peptide substrate, the AAF-GLO substrate, to measure dead-cell protease activity, which is released from cells that have lost membrane integrity, resulting in the generation of a "glow-type" luminescent signal that is proportional to the number of dead cells in the sample. The AAF-GLO substrate cannot cross the intact membrane of live cells and does not generate any appreciable signal from the live-cell population. In these assays, TCR engineered PBL were co-incubated with increasing ratios of target cells (E:T) in AIM-V medium in 96-well U-bottom plates at 37° C. for 4 hours (hr.) Lysis was measured by bioluminescence release in the medium: percent specific lysis=[specific release−(spontaneous effector release+spontaneous target release)]/total target release−spontaneous target release× 100%, average of quadruplicate samples. Little or no cell lysis is measured as a negative value.

As shown in Table 21, both mTCR and hTCR transduced PBL demonstrated similar lytic activity against melanoma NY-ESO-1$^+$/HLA-A*0201$^+$ tumor cell line 624.38mel. There was little or no lysis of HLA-A*0201$^-$ cell line 938 mel, and the GFP transduced PBL showed no reactivity against any of the target cells (Table 21).

TABLE 21

| | Effector:target ratio | | |
|---|---|---|---|
| | 10:1 | 30:1 | 60:1 |
| | Positive Target: 624.38 cells | | |
| GFP | −9 | −3 | −2 |
| 1G4-LY TCR | 29 | 59 | 58 |
| mESOβα TCR | 31 | 59 | 60 |
| | Negative Target: 938 cells | | |
| GFP | −19 | −22 | −34 |
| 1G4-LY TCR | −13 | −11 | −10 |
| mESOβα TCR | −13 | −10 | −10 |

Example 17

This example demonstrates the anti-tumor activity of cells transduced with a mESOβα TCR or human TCR using a retroviral supernatant from the packaging cell clone of Example 13.

The anti-tumor activity of CD4+ T lymphocytes transduced with the mTCR and the hTCR was also investigated. NY-ESO-1 hTCR and NY-ESO-1 mTCR transduced PBL were enriched with CD4+ magnetic beads, then co-cultured for 16 hours with a panel of HLA-A*0201$^+$ and HLA-A*0201$^-$ melanoma and lung tumor derived cell lines. CD4+ T lymphocytes transduced with both the mTCR and the hTCR had specific release of IFN-γ when co-cultured with HLA-A*0201$^+$/NY-ESO-1$^+$ cell lines but not HLA-A*0201$^-$/NY-ESO-1$^+$ cell lines (Table 22).

TABLE 22

| | H1299A2 | 624.38 | 938 |
|---|---|---|---|
| | IFN-γ pg/ml (Donor I) | | |
| Untransduced | 0 | 31 | 0 |
| 1G4-LY TCR | 22684 | 7020 | 0 |
| mESOβα TCR | 21376 | 3754 | 41 |
| | IFN-γ pg/ml (Donor J) | | |
| Untransduced | 1158 | 0 | 0 |
| 1G4-LY TCR | 22786 | 2594 | 0 |
| mESOβα TCR | 22331 | 481 | 14 |

Example 18

This example demonstrates the specific recognition of different tumor histologies by cells transduced with a mESOβα TCR using a retroviral supernatant from the packaging cell clone of Example 13.

To assess the specific recognition of various tumor histologies, NY-ESO-1 mTCR transduced PBL were co-cultured with different HLA-A*0201$^+$/NY-ESO-1$^+$ cell lines derived from melanoma (A375), non-small cell lung cancer (H1299-A2), neuroblastoma (SKN AS-A2), breast cancer (MDA-435S-A2), and osteosarcoma (Saos2). Specific release of IFN-γ was observed (Table 23).

TABLE 23

| | IFN-γ pg/ml | |
|---|---|---|
| | Untransduced | mESOβα TCR |
| A375 | 0 | 5710 |
| H1299-A2 | 132 | 21222 |
| MDA-435S-A2 | 1181 | 3057 |
| SKN AS-A2 | 1417 | 5097 |
| Saos2 | 117 | 12092 |

Example 19

This example demonstrates the recognition of DAC-treated tumor cells by PBL transduced with a mESOβα TCR.

Increasing concentrations of the DNA-demethylating agent 5-aza-2'-deoxycytidine (decitabine; DAC) induces expression of various cancer testis antigens in lung cancer cells (Rao et al., *Ther. Tar. and Chem. Bio.*, 71: 4192-4204 (2011)). Without being bound to a particular theory or mechanism, it is believed that DAC may, potentially, up-regulate NY-ESO-1 expression in cancer cells, which may enhance the ability of the TCRs to recognize NY-ESO-1.

NY-ESO-1 mTCR transduced or untransduced PBL were co-cultured for 16 hours with the tumor target cell lines of different histologies (shown in Tables 24A-24B) that had been exposed to DAC at the concentrations shown in Tables 24A-24B for 72 hours. Interferon-gamma levels were measured. The results are shown in Table 24A-24B.

TABLE 24A

| Prostate Cancer (pC3A2 cells) | | |
|---|---|---|
| | IFN-γ (pg/ml) | |
| DAC concentration (mM/L) | Untransduced | mESOβα TCR from Clone C1 |
| Untreated | 159 | 336 |
| 0.1 | 289 | 1566 |
| 0.5 | 188 | 1766 |
| 1.0 | 282 | 1912 |
| 10 | 361 | 1520 |

TABLE 24B

| Colorectal Cancer (SW480 cells) | | |
|---|---|---|
| | IFN-γ (pg/ml) | |
| DAC concentration (mM/L) | Untransduced | mESOβα TCR from Clone C1 |
| Untreated | 118 | 135 |
| 0.1 | 141 | 196 |
| 0.5 | 169 | 239 |
| 1.0 | 98 | 255 |
| 10 | 80 | 388 |

As shown in Tables 24A and 24B, the PBL transduced with mESOβα TCR demonstrated higher reactivity toward DAC-treated target prostate cancer and colorectal cancer, respectively, as compared to untreated target cells.

Example 20

This example demonstrates the recognition of T2 cells pulsed with alanine-substituted NY-ESO-1 peptides by PBL transduced with the mESON TCR or human TCR.

Untransduced human PBL or human PBL transduced with mTCR (mESOβα from clone C1), hTCR (1G4-LY TCR), or green fluorescent protein (GFP) were co-cultured for 16 hours with untreated T2 cells or T2 cells that were previously pulsed with different concentrations of peptide as shown in Tables 25A and 25B. Interferon gamma was measured. The results are shown in Table 25A and 25B. As shown in Tables 25A and 25B, the mTCR recognizes SEQ ID NO: 24 while the hTCR does not. In addition, the hTCR recognizes SEQ ID NO: 27 but the mTCR does not.

TABLE 25A

| (Donor K) | | | | | |
|---|---|---|---|---|---|
| | | IFN-γ (pg/ml) | | | |
| pulsed peptide | (ng/μL) | Untransduced | GFP | 1G4-LY TCR | mESOβα |
| untreated T2 Cells | — | 943 | 358 | 641 | 443 |
| SLLMWITQC (SEQ ID NO: 2) | 10 | 0 | 0 | 3759 | 5741 |
| SLLMWITQC (SEQ ID NO: 2) | 1 | 0 | 0 | 678 | 2111 |
| MART | 10 | 0 | 0 | 0 | 0 |
| MART | 1 | 0 | 0 | 0 | 0 |
| SLAMWITQC (SEQ ID NO: 23) | 10 | 0 | 0 | 3271 | 6287 |
| SLAMWITQC (SEQ ID NO: 23) | 1 | 0 | 0 | 1785 | 2421 |
| SLLAWITQC (SEQ ID NO: 24) | 10 | 0 | 0 | 0 | 2701 |
| SLLAWITQC (SEQ ID NO: 24) | 1 | 0 | 0 | 0 | 3172 |
| SLLMAITQC (SEQ ID NO: 25) | 10 | 0 | 0 | 0 | 0 |
| SLLMAITQC (SEQ ID NO: 25) | 1 | 0 | 0 | 0 | 0 |
| SLLMWATQC (SEQ ID NO: 26) | 10 | 0 | 0 | 1114 | 1194 |
| SLLMWATQC (SEQ ID NO: 26) | 1 | 0 | 0 | 884 | 921 |
| SLLMWIAQC (SEQ ID NO: 27) | 10 | 0 | 0 | 5672 | 0 |
| SLLMWIAQC (SEQ ID NO: 27) | 1 | 0 | 0 | 457 | 0 |
| SLLMWITAC (SEQ ID NO: 28) | 10 | 0 | 0 | 0 | 0 |
| SLLMWITAC (SEQ ID NO: 28) | 1 | 0 | 0 | 0 | 0 |

TABLE 25B (Donor L)

| pulsed peptide | (ng/μL) | IFN-γ (pg/ml) | | | |
|---|---|---|---|---|---|
| | | Untransduced | GFP | 1G4-LY TCR | mESOβα |
| untreated T2 Cells | — | 162 | 126 | 131 | 188 |
| SLLMWITQC (SEQ ID NO: 2) | 10 | 124 | 120 | 754 | 1168 |
| SLLMWITQC (SEQ ID NO: 2) | 1 | 199 | 112 | 184 | 273 |
| MART | 10 | 230 | 136 | 123 | 102 |
| MART | 1 | 155 | 152 | 112 | 108 |
| SLAMWITQC (SEQ ID NO: 23) | 10 | 145 | 168 | 1383 | 1541 |
| SLAMWITQC (SEQ ID NO: 23) | 1 | 120 | 139 | 370 | 505 |
| SLLAWITQC (SEQ ID NO: 24) | 10 | 128 | 121 | 185 | 616 |
| SLLAWITQC (SEQ ID NO: 24) | 1 | 123 | 111 | 225 | 1000 |
| SLLMAITQC (SEQ ID NO: 25) | 10 | 183 | 163 | 294 | 137 |
| SLLMAITQC (SEQ ID NO: 25) | 1 | 119 | 112 | 148 | 214 |
| SLLMWATQC (SEQ ID NO: 26) | 10 | 96 | 80 | 297 | 375 |
| SLLMWATQC (SEQ ID NO: 26) | 1 | 74 | 70 | 220 | 280 |
| SLLMWIAQC (SEQ ID NO: 27) | 10 | 78 | 95 | 1026 | 76 |
| SLLMWIAQC (SEQ ID NO: 27) | 1 | 123 | 72 | 208 | 86 |
| SLLMWITAC (SEQ ID NO: 28) | 10 | 78 | 83 | 97 | 76 |
| SLLMWITAC (SEQ ID NO: 28) | 1 | 85 | 75 | 82 | 74 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated or purified T-cell receptor (TCR) having antigenic specificity for NY-ESO-1 (SEQ ID NO: 1) and comprising a murine variable region, wherein the TCR comprises the amino acid sequences of SEQ ID NOs: 3-8.

2. The isolated or purified TCR according to claim 1, wherein the TCR has antigenic specificity for NY-ESO-1$_{157-165}$ (SEQ ID NO: 2).

3. The isolated or purified TCR according to claim 1, comprising the amino acid sequences of SEQ ID NOs: 9 and 10.

4. The isolated or purified TCR according to claim 1, comprising the amino acid sequences of SEQ ID NOs: 11 and 12.

5. An isolated or purified polypeptide comprising the amino acid sequences of SEQ ID NOs: 3-8.

6. The isolated or purified polypeptide of claim 5, comprising the amino acid sequences of both SEQ ID NOs: 9 and 10.

7. The isolated or purified polypeptide of claim 5, comprising the amino acid sequences of both SEQ ID NOs: 11 and 12.

8. An isolated or purified protein comprising the polypeptide of claim 5.

9. An isolated or purified protein comprising a first polypeptide chain comprising the amino acid sequences of SEQ ID NOs: 3-5 and a second polypeptide chain comprising the amino acid sequences of SEQ ID NOs: 6-8.

10. The isolated or purified protein according to claim 9, comprising a first polypeptide chain comprising the amino acid sequence of SEQ ID NO: 9 and a second polypeptide chain comprising the amino acid sequence of SEQ ID NO: 10.

11. The isolated or purified protein according to claim 9, comprising a first polypeptide chain comprising the amino acid sequence of SEQ ID NO: 11 and a second polypeptide chain comprising the amino acid sequence of SEQ ID NO: 12.

12. The isolated or purified protein of claim 8, wherein the protein is a fusion protein.

13. The isolated or purified protein of claim 8, wherein the protein is a recombinant antibody.

14. An isolated or purified nucleic acid comprising a nucleotide sequence encoding the TCR according to claim 1.

15. The isolated or purified nucleic acid according to claim 14, wherein the nucleotide sequence is codon-optimized.

16. The isolated or purified nucleic acid according to claim 14, wherein the nucleotide sequence comprises both of SEQ ID NOs: 15 and 16 or both of SEQ ID NOs: 19 and 20.

17. A recombinant expression vector comprising the nucleic acid according to claim 14.

18. The recombinant expression vector according to claim 17, wherein the nucleotide sequence comprises a nucleotide sequence encoding a complementarity determining region (CDR) 1α, CDR2α, CDR3α, CDR1β, CDR2β, and CDR3β, and the nucleotide sequence encoding the CDR1α, CDR2α, and CDR3α is 5' of the nucleotide sequence encoding the CDR1β, CDR2β, and CDR3β.

19. The recombinant expression vector according to claim 17, wherein the nucleotide sequence comprises a nucleotide sequence encoding a CDR 1α, CDR2α, CDR3α, CDR1β, CDR2β, and CDR3β, and the nucleotide sequence encoding the CDR1α, CDR2α, and CDR3α is 3' of the nucleotide sequence encoding the CDR1β, CDR2β, and CDR3β.

20. The recombinant expression vector according to claim 18, comprising SEQ ID NO: 17.

21. The recombinant expression vector according to claim 19, comprising SEQ ID NO: 18.

22. An isolated host cell comprising the recombinant expression vector of claim 17.

23. The host cell according to claim 22, wherein the cell is human.

24. A population of cells comprising at least one host cell of claim 22.

25. A pharmaceutical composition comprising the TCR according to claim 1, and a pharmaceutically acceptable carrier.

26. A method of detecting the presence of cancer in a mammal, comprising:
  (a) contacting a sample comprising one or more cells from the mammal with the TCR according to claim 1, thereby forming a complex, and
  (b) detecting the complex, wherein detection of the complex is indicative of the presence of cancer in the mammal;
  wherein the cancer is melanoma, breast cancer, lung cancer, prostate cancer, thyroid cancer, ovarian cancer, or synovial cell sarcoma.

27. A method of treating melanoma in a mammal, the method comprising administering to the mammal the TCR according to claim 1 in an amount effective to treat melanoma in a mammal.

* * * * *

SEQUENCE LISTING

<160> NUMBER OF SEQ ID NOS: 28

<210> SEQ ID NO 1
<211> LENGTH: 180
<212> TYPE: PRT
<213> ORGANISM: Homo sapiens

<400> SEQUENCE: 1

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Gly Gly Ala Pro Arg Gly Pro
    50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
        115                 120                 125

Ser Gly Asn Ile Leu Thr Ile Arg Leu Thr Ala Ala Asp His Arg Gln
    130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
            180

<210> SEQ ID NO 2
<211> LENGTH: 9
<212> TYPE: PRT
<213> ORGANISM: Homo sapiens

<400> SEQUENCE: 2

Ser Leu Leu Met Trp Ile Thr Gln Cys
1               5

<210> SEQ ID NO 3
<211> LENGTH: 8
<212> TYPE: PRT
<213> ORGANISM: Mus musculus

<400> SEQUENCE: 3

Ala Thr Ser Ile Gly Tyr Pro Asn
1               5

<210> SEQ ID NO 4
<211> LENGTH: 7
<212> TYPE: PRT
<213> ORGANISM: Mus musculus

<400> SEQUENCE: 4

Val Ile Thr Ala Gly Gln Lys
1               5

<210> SEQ ID NO 5
<211> LENGTH: 12
<212> TYPE: PRT
<213> ORGANISM: Mus musculus

<400> SEQUENCE: 5

Cys Ala Leu Trp Ser Gly Ser Trp Gln Leu Ile Phe
1               5                   10

<210> SEQ ID NO 6
<211> LENGTH: 5
<212> TYPE: PRT
<213> ORGANISM: Mus musculus

<400> SEQUENCE: 6

Lys Gly His Pro Val
1               5

<210> SEQ ID NO 7
<211> LENGTH: 6
<212> TYPE: PRT
<213> ORGANISM: Mus musculus

<400> SEQUENCE: 7

Phe Gln Asn Gln Glu Val
1               5

<210> SEQ ID NO 8
<211> LENGTH: 11
<212> TYPE: PRT
<213> ORGANISM: Mus musculus

<400> SEQUENCE: 8

Cys Ala Ser Arg Asp Ser Pro Glu Gln Tyr Phe
1               5                   10

<210> SEQ ID NO 9
<211> LENGTH: 136
<212> TYPE: PRT
<213> ORGANISM: Mus musculus

<400> SEQUENCE: 9

Met Thr Leu Lys Met Asp Ser Ser Pro Gly Phe Val Ala Val Ile Leu
1               5                   10                  15

Leu Ile Leu Gly Arg Thr His Gly Asp Ser Val Thr Gln Thr Glu Gly
                20                  25                  30

Gln Val Thr Val Ser Glu Ser Lys Ser Leu Ile Ile Asn Cys Thr Tyr
            35                  40                  45

Ser Ala Thr Ser Ile Gly Tyr Pro Asn Leu Phe Trp Tyr Val Arg Tyr
        50                  55                  60

Pro Gly Glu Gly Leu Gln Leu Leu Lys Val Ile Thr Ala Gly Gln
65                  70                  75                  80

Lys Gly Ser Ser Arg Gly Phe Glu Ala Thr Tyr Asn Lys Glu Ala Thr
                85                  90                  95

Ser Phe His Leu Gln Lys Ala Ser Val Gln Glu Ser Asp Ser Ala Val
            100                 105                 110

Tyr Tyr Cys Ala Leu Trp Ser Gly Ser Trp Gln Leu Ile Phe Gly Ser
        115                 120                 125

Gly Thr Gln Leu Thr Val Met Pro
    130                 135

```
<210> SEQ ID NO 10
<211> LENGTH: 131
<212> TYPE: PRT
<213> ORGANISM: Mus musculus

<400> SEQUENCE: 10

Met Ala Thr Arg Leu Leu Cys Tyr Thr Val Leu Cys Leu Leu Gly Ala
1               5                   10                  15

Arg Ile Leu Asn Ser Lys Val Ile Gln Thr Pro Arg Tyr Leu Val Lys
            20                  25                  30

Gly Gln Gly Gln Lys Ala Lys Met Arg Cys Ile Pro Glu Lys Gly His
        35                  40                  45

Pro Val Val Phe Trp Tyr Gln Gln Asn Lys Asn Asn Glu Phe Lys Phe
    50                  55                  60

Leu Ile Asn Phe Gln Asn Gln Glu Val Leu Gln Gln Ile Asp Met Thr
65                  70                  75                  80

Glu Lys Arg Phe Ser Ala Glu Cys Pro Ser Asn Ser Pro Cys Ser Leu
                85                  90                  95

Glu Ile Gln Ser Ser Glu Ala Gly Asp Ser Ala Leu Tyr Leu Cys Ala
            100                 105                 110

Ser Arg Asp Ser Pro Glu Gln Tyr Phe Gly Pro Gly Thr Arg Leu Thr
        115                 120                 125

Val Leu Glu
    130

<210> SEQ ID NO 11
<211> LENGTH: 273
<212> TYPE: PRT
<213> ORGANISM: Mus musculus

<400> SEQUENCE: 11

Met Thr Leu Lys Met Asp Ser Ser Pro Gly Phe Val Ala Val Ile Leu
1               5                   10                  15

Leu Ile Leu Gly Arg Thr His Gly Asp Ser Val Thr Gln Thr Glu Gly
            20                  25                  30

Gln Val Thr Val Ser Glu Ser Lys Ser Leu Ile Ile Asn Cys Thr Tyr
        35                  40                  45

Ser Ala Thr Ser Ile Gly Tyr Pro Asn Leu Phe Trp Tyr Val Arg Tyr
    50                  55                  60

Pro Gly Glu Gly Leu Gln Leu Leu Lys Val Ile Thr Ala Gly Gln
65                  70                  75                  80

Lys Gly Ser Ser Arg Gly Phe Glu Ala Thr Tyr Asn Lys Glu Ala Thr
                85                  90                  95

Ser Phe His Leu Gln Lys Ala Ser Val Gln Glu Ser Asp Ser Ala Val
            100                 105                 110

Tyr Tyr Cys Ala Leu Trp Ser Gly Ser Trp Gln Leu Ile Phe Gly Ser
        115                 120                 125

Gly Thr Gln Leu Thr Val Met Pro Asp Ile Gln Asn Pro Glu Pro Ala
    130                 135                 140

Val Tyr Gln Leu Lys Asp Pro Arg Ser Gln Asp Ser Thr Leu Cys Leu
145                 150                 155                 160

Phe Thr Asp Phe Asp Ser Gln Ile Asn Val Pro Lys Thr Met Glu Ser
                165                 170                 175

Gly Thr Phe Ile Thr Asp Lys Val Leu Asp Met Lys Ala Met Asp
            180                 185                 190
```

```
Ser Lys Ser Asn Gly Ala Ile Ala Trp Ser Asn Gln Thr Ser Phe Thr
        195                 200                 205

Cys Gln Asp Ile Phe Lys Glu Thr Asn Ala Thr Tyr Pro Ser Ser Asp
    210                 215                 220

Val Pro Cys Asp Ala Thr Leu Thr Glu Lys Ser Phe Glu Thr Asp Met
225                 230                 235                 240

Asn Leu Asn Phe Gln Asn Leu Ser Val Met Gly Leu Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 12
<211> LENGTH: 303
<212> TYPE: PRT
<213> ORGANISM: Mus musculus

<400> SEQUENCE: 12

Met Ala Thr Arg Leu Leu Cys Tyr Thr Val Leu Cys Leu Leu Gly Ala
1               5                   10                  15

Arg Ile Leu Asn Ser Lys Val Ile Gln Thr Pro Arg Tyr Leu Val Lys
            20                  25                  30

Gly Gln Gly Gln Lys Ala Lys Met Arg Cys Ile Pro Glu Lys Gly His
        35                  40                  45

Pro Val Val Phe Trp Tyr Gln Gln Asn Lys Asn Asn Glu Phe Lys Phe
    50                  55                  60

Leu Ile Asn Phe Gln Asn Gln Glu Val Leu Gln Ile Asp Met Thr
65                  70                  75                  80

Glu Lys Arg Phe Ser Ala Glu Cys Pro Ser Asn Ser Pro Cys Ser Leu
                85                  90                  95

Glu Ile Gln Ser Ser Glu Ala Gly Asp Ser Ala Leu Tyr Leu Cys Ala
            100                 105                 110

Ser Arg Asp Ser Pro Glu Gln Tyr Phe Gly Pro Gly Thr Arg Leu Thr
        115                 120                 125

Val Leu Glu Asp Leu Arg Asn Val Thr Pro Pro Lys Val Ser Leu Phe
    130                 135                 140

Glu Pro Ser Lys Ala Glu Ile Ala Asn Lys Gln Lys Ala Thr Leu Val
145                 150                 155                 160

Cys Leu Ala Arg Gly Phe Phe Pro Asp His Val Glu Leu Ser Trp Trp
                165                 170                 175

Val Asn Gly Lys Glu Val His Ser Gly Val Ser Thr Asp Pro Gln Ala
            180                 185                 190

Tyr Lys Glu Ser Asn Tyr Ser Tyr Cys Leu Ser Ser Arg Leu Arg Val
        195                 200                 205

Ser Ala Thr Phe Trp His Asn Pro Arg Asn His Phe Arg Cys Gln Val
    210                 215                 220

Gln Phe His Gly Leu Ser Glu Glu Asp Lys Trp Pro Glu Gly Ser Pro
225                 230                 235                 240

Lys Pro Val Thr Gln Asn Ile Ser Ala Glu Ala Trp Gly Arg Ala Asp
                245                 250                 255

Cys Gly Ile Thr Ser Ala Ser Tyr His Gln Gly Val Leu Ser Ala Thr
            260                 265                 270

Ile Leu Tyr Glu Ile Leu Leu Gly Lys Ala Thr Leu Tyr Ala Val Leu
        275                 280                 285
```

```
Val Ser Gly Leu Val Leu Met Ala Met Val Lys Lys Lys Asn Ser
    290                 295                 300
```

<210> SEQ ID NO 13
<211> LENGTH: 27
<212> TYPE: PRT
<213> ORGANISM: Artificial Sequence
<220> FEATURE:
<223> OTHER INFORMATION: Synthetic

<400> SEQUENCE: 13

```
Arg Ala Lys Arg Ser Gly Ser Gly Ala Thr Asn Phe Ser Leu Leu Lys
1               5                   10                  15

Gln Ala Gly Asp Val Glu Glu Asn Pro Gly Pro
            20                  25
```

<210> SEQ ID NO 14
<211> LENGTH: 81
<212> TYPE: DNA
<213> ORGANISM: Artificial Sequence
<220> FEATURE:
<223> OTHER INFORMATION: Synthetic

<400> SEQUENCE: 14

| | | |
|---|---|---|
| agggccaaac gctcagggag cggagctacc aattttctc tgctgaagca ggccggcgat | 60 |
| gtggaggaaa atcctgggcc a | 81 |

<210> SEQ ID NO 15
<211> LENGTH: 825
<212> TYPE: DNA
<213> ORGANISM: Artificial Sequence
<220> FEATURE:
<223> OTHER INFORMATION: Synthetic

<400> SEQUENCE: 15

| | |
|---|---|
| atgacactga aaatggactc aagccctgga ttcgtggctg tcatcctgct gattctgggc | 60 |
| cggactcacg gggatagcgt gacccagaca gagggccagg tgaccgtctc cgaatctaag | 120 |
| agtctgatca ttaactgtac ctactccgcc acatctatcg ggtatcctaa tctgttctgg | 180 |
| tacgtgcgct atccaggcga ggggctgcag ctgctgctga agtcattac cgctgggcag | 240 |
| aagggatcct ctcgaggatt cgaggcaaca taacaaag aagccacttc atttcatctg | 300 |
| cagaaggcaa gcgtgcagga atcagatagc gccgtgtact attgcgcact gtggtccggc | 360 |
| tcttggcagc tgatctttgg atccggcacc cagctgacag tgatgcccga cattcagaac | 420 |
| cccgagcctg ccgtctatca gctgaaggac cctcgaagtc aggatagcac cctgtgcctg | 480 |
| ttcaccgact tgattcccga tcaatgtgt cccaaaacaa tggaatctgg cactttcatt | 540 |
| accgacaaga cagtcctgga tatgaaagct atggacagta agtcaaacgg ggcaatcgcc | 600 |
| tggagcaatc agacttcctt cacctgccag gatatcttca ggagacaaa cgcaacttac | 660 |
| cccagttcag acgtgccttg tgatgccact ctgaccgaga agagcttcga accgacatg | 720 |
| aacctgaatt ttcagaatct gagcgtgatg ggcctgcgca tcctgctgct gaaggtggct | 780 |
| gggttcaatc tgctgatgac actgagactg tggagtagtt gataa | 825 |

<210> SEQ ID NO 16
<211> LENGTH: 909
<212> TYPE: DNA
<213> ORGANISM: Artificial Sequence
<220> FEATURE:
<223> OTHER INFORMATION: Synthetic

<400> SEQUENCE: 16

| | | | | | |
|---|---|---|---|---|---|
| atggccacac | gcctgctgtg | ctacactgtg | ctgtgcctgc | tgggggctcg | catcctgaac | 60 |
| tcaaaagtca | tccagacacc | tcgctacctg | gtcaaaggcc | aggggcagaa | agccaagatg | 120 |
| agatgcatcc | ctgagaaggg | gcacccagtg | gtcttctggt | accagcagaa | caaaaacaat | 180 |
| gagttcaagt | ttctgatcaa | ctttcagaat | caggaagtgc | tgcagcagat | tgatatgacc | 240 |
| gagaagcggt | tctcagccga | atgcccaagc | aattccccct | gtagcctgga | gatccagagc | 300 |
| tccgaagccg | gcgatagcgc | cctgtacctg | tgcgctagca | gagactcccc | agagcagtat | 360 |
| tttggacccg | gcacaagact | gactgtgctg | gaagacctga | ggaacgtgac | tccccctaaa | 420 |
| gtctctctgt | tcgagcctag | taaggctgaa | atcgcaaaca | gcagaaggc | caccctggtg | 480 |
| tgcctggcta | ggggcttctt | tccagatcac | gtggagctgt | cctggtgggt | caacgggaaa | 540 |
| gaagtgcatt | ctggagtcag | tacagacccc | caggcttaca | aggagtcaaa | ttacagctat | 600 |
| tgcctgtcta | gtcggctgag | agtgtctgca | acttttggc | acaacccacg | aaatcatttc | 660 |
| cggtgtcagg | tgcagtttca | cggactgtcc | gaggaagata | aatggcccga | gggctctcca | 720 |
| aagcccgtga | cacagaacat | cagtgccgaa | gcttgggac | gagctgactg | cggaattact | 780 |
| tctgcaagtt | atcatcaggg | cgtgctgtcc | gcaaccatcc | tgtacgagat | tctgctgggg | 840 |
| aaggcaacac | tgtatgccgt | gctggtcagt | ggactggtgc | tgatggctat | ggtgaagaag | 900 |
| aagaacagc | | | | | 909 |

<210> SEQ ID NO 17
<211> LENGTH: 1815
<212> TYPE: DNA
<213> ORGANISM: Artificial Sequence
<220> FEATURE:
<223> OTHER INFORMATION: Synthetic

<400> SEQUENCE: 17

| | | | | | |
|---|---|---|---|---|---|
| atggccctga | aaatggactc | tagccctggg | tttgtcgccg | tcatcctgct | gatcctgggg | 60 |
| agaactcacg | gagatagcgt | cactcagacc | gaaggacagg | tgacagtcag | cgagtccaag | 120 |
| tctctgatca | ttaactgcac | atacagcgcc | acttccatcg | gctatcctaa | tctgttttgg | 180 |
| tacgtgaggt | atccaggcga | agggctgcag | ctgctgctga | aggtcattac | tgctgggcag | 240 |
| aaaggaagct | cccgcggctt | cgaggctact | tacaacaagg | aagcaacctc | atttcacctg | 300 |
| cagaaagcaa | gcgtgcagga | gagtgattca | gcagtctact | attgcgcact | gtggagcgga | 360 |
| tcctggcagc | tgatctttgg | aagcggcact | cagctgaccg | tgatgcccga | cattcagaac | 420 |
| ccagagcccg | ccgtctatca | gctgaaggac | cctaggtctc | aggatagcac | cctgtgcctg | 480 |
| ttcacagact | tgattcaca | gatcaatgtg | cctaagacaa | tggagtccgg | cacattcatt | 540 |
| actgacaaaa | ccgtcctgga | tatgaaggct | atggactcta | aaagtaacgg | ggccatcgct | 600 |
| tggagcaatc | agacatcctt | cacttgccag | gatatcttca | aggagaccaa | cgccacatac | 660 |
| ccttctagtg | acgtgccatg | tgatgctacc | ctgacagaga | aaagcttcga | aaccgacatg | 720 |
| aacctgaatt | ttcagaacct | gtccgtgatg | ggcctgcgga | tcctgctgct | gaaggtcgcc | 780 |
| gggtttaatc | tgctgatgac | tctgagactg | tggtcaagca | gggcaaagcg | gagcggaagc | 840 |
| ggagcaacca | acttctctct | gctgaaacag | gcaggggatg | tggaggaaaa | tcctggacca | 900 |
| atggccacac | ggctgctgtg | ctacaccgtg | ctgtgcctgc | tgggagcacg | catcctgaat | 960 |
| agcaaagtga | tccagacacc | ccgatatctg | gtcaaaggcc | aggggcagaa | ggccaaaatg | 1020 |
| agatgcatcc | ccgagaaggg | acatcctgtg | gtcttctggt | atcagcagaa | caagaacaac | 1080 |

```
gagttcaaat ttctgatcaa cttccagaat caggaagtgc tgcagcagat tgatatgacc    1140
gagaaacgat tctctgccga atgcccatcc aattctccct gtagtctgga gatccagtcc    1200
tctgaagccg gcgatagcgc cctgtacctg tgcgcttcac gcgacagccc agagcagtat    1260
tttggacccg gcactagact gaccgtgctg aagacctga ggaacgtgac ccccctaag     1320 gtctctctgt tcgagcctag taaagctgaa attgcaaata agcagaaagc caccctggtg    1380
tgcctggcta ggggcttctt tccagatcac gtggagctgt cctggtgggt caacggaaag    1440
gaagtgcatt ccggcgtctc tactgacccc caggcctaca agagagtaa ttactcatat     1500 tgcctgagtt cacggctgag agtgtctgct accttctggc acaacccacg aaatcatttc    1560
cggtgtcagg tgcagtttca cggactgtcc gaggaggata gtggcccga gggctctccc     1620 aaacctgtga cacagaacat cagtgcagaa gcatggggac gagctgactg tggaattact    1680
agtgcatcat accatcaggg ggtgctgtcc gctaccatcc tgtatgagat tctgctggga    1740
aaggcaacac tgtatgctgt gctggtgtct gggctggtgc tgatggctat ggtgaaaaag    1800
aagaactcat gataa                                                      1815

<210> SEQ ID NO 18
<211> LENGTH: 1815
<212> TYPE: DNA
<213> ORGANISM: Artificial Sequence
<220> FEATURE:
<223> OTHER INFORMATION: Synthetic

<400> SEQUENCE: 18
atggccacac gcctgctgtg ctacactgtg ctgtgcctgc tgggggctcg catcctgaac      60
tcaaaagtca tccagacacc tcgctacctg gtcaaaggcc aggggcagaa agccaagatg    120
agatgcatcc ctgagaaggg gcacccgtg gtcttctggt accagcagaa caaaaacaat      180
gagttcaagt ttctgatcaa ctttcagaat caggaagtgc tgcagcagat tgatatgacc    240
gagaagcggt tctcagccga atgcccaagc aattcccct gtagcctgga gatccagagc     300
tccgaagccg gcgatagcgc cctgtacctg tgcgctagca gagactcccc agagcagtat    360
tttggacccg gcacaagact gactgtgctg aagacctga ggaacgtgac tccccctaaa    420
gtctctctgt tcgagcctag taaggctgaa atcgcaaaca agcagaaggc caccctggtg    480
tgcctggcta ggggcttctt tccagatcac gtggagctgt cctggtgggt caacgggaaa    540
gaagtgcatt ctggagtcag tacagacccc caggcttaca aggagtcaaa ttacagctat    600
tgcctgtcta gtcggctgag agtgtctgca acttttggc acaacccacg aaatcatttc    660
cggtgtcagg tgcagtttca cggactgtcc gaggaagata atgggcccga gggctctcca    720
aagcccgtga cacagaacat cagtgccgaa gcttggggac gagctgactg cggaattact    780
tctgcaagtt atcatcaggg cgtgctgtcc gcaaccatcc tgtacgagat tctgctgggg    840
aaggcaacac tgtatgccgt gctggtcagt ggactggtgc tgatggctat ggtgaagaag    900
aagaacagca gggccaaacg ctcagggagc ggagctacca ttttttctct gctgaagcag    960
gccggcgatg tggaggaaaa tcctgggcca atgacactga aaatggactc aagccctgga    1020
ttcgtggctg tcatcctgct gattctgggc cggactcacg gggatagcgt gacccagaca    1080
gagggccagg tgaccgtctc cgaatctaag agtctgatca ttaactgtac ctactccgcc    1140
acatctatcg ggatcctaa tctgttctgg tacgtcgct atccaggcga ggggctgcag    1200
ctgctgctga aagtcattac cgctgggcag aagggatcct ctcgaggatt cgaggcaaca    1260
```

```
tacaacaaag aagccacttc atttcatctg cagaaggcaa gcgtgcagga atcagatagc   1320
gccgtgtact attgcgcact gtggtccggc tcttggcagc tgatctttgg atccggcacc   1380
cagctgacag tgatgcccga cattcagaac cccgagcctg ccgtctatca gctgaaggac   1440
cctcgaagtc aggatagcac cctgtgcctg ttcaccgact tgattcccca gatcaatgtg   1500
cccaaaacaa tggaatctgg cactttcatt accgacaaga cagtcctgga tatgaaagct   1560
atggacagta agtcaaacgg ggcaatcgcc tggagcaatc agacttcctt cacctgccag   1620
gatatcttca aggagacaaa cgcaacttac cccagttcag acgtgccttg tgatgccact   1680
ctgaccgaga gagcttcga aaccgacatg aacctgaatt ttcagaatct gagcgtgatg   1740
ggcctgcgca tcctgctgct gaaggtggct gggttcaatc tgctgatgac actgagactg   1800
tggagtagtt gataa                                                   1815

<210> SEQ ID NO 19
<211> LENGTH: 822
<212> TYPE: DNA
<213> ORGANISM: Mus musculus

<400> SEQUENCE: 19 atgcactaa agatggactc ttctccaggc ttcgtggctg tgatacttct catactggga     60
aggacccatg gagattccgt gactcaaaca gaaggccaag tgactgtctc agaaagcaag   120
tccctgataa taaattgcac gtattcagcc acaagcatag gttaccctaa tcttttctgg   180
tatgttcgat atcctggaga aggtctacaa ctcctcctga agtcattac ggctggccag    240 aagggaagca gcagagggtt tgaagccaca tacaataaag aagccacctc cttccacttg   300
cagaaagcct cagtgcaaga gtcagactcg gctgtgtact actgcgctct gtggtctggc   360
agctggcaac tcatctttgg atctggaacc caactgacag ttatgcctga catccagaac   420
ccagaacctg ctgtgtacca gttaaaagat cctcggtctc aggacagcac cctctgcctg   480
ttcaccgact tgactcccca atcaatgtg ccgaaaacca tggaatctgg aacgttcatc    540
actgacaaaa ctgtgctgga catgaaagct atggattcca agagcaatgg ggccattgcc   600
tggagcaacc agacaagctt cacctgccaa gatatcttca agagaccaa cgccacctac    660 cccagttcag acgttccctg tgatgccacg ttgactgaga aaagctttga acagatatg    720 aacctaaact tcaaaacct gtcagttatg ggactccgaa tcctcctgct gaaagtagcc   780
ggatttaacc tgctcatgac gctgaggctg tggtccagtt ga                     822

<210> SEQ ID NO 20
<211> LENGTH: 912
<212> TYPE: DNA
<213> ORGANISM: Mus musculus

<400> SEQUENCE: 20
atggctacaa ggctcctctg ttacacagta ctttgtctcc tgggtgcaag aattttgaat    60
tcaaaagtca ttcagactcc aagatatctg gtgaaagggc aaggacaaaa agcaaagatg   120
aggtgtatcc ctgaaaaggg acatccagtt gtattctggt atcaacaaaa taagaacaat   180
gagtttaaat ttttgattaa cttttcagaat caagaagttc ttcagcaaat agacatgact   240
gaaaaacgat tctctgctga gtgtccttca aactcacctt gcagcctaga aattcagtcc   300
tctgaggcag agactcagc actgtacctc tgtgccagca gggacagtcc tgaacagtac   360
ttcggtcccg gcaccaggct cacgttttta gaggatctga aaatgtgac tccacccaag   420 gtctccttgt ttgagccatc aaaagcagag attgcaaaca acaaaaggc taccctcgtg   480
```

```
tgcttggcca gggcttcttt ccctgaccac gtggagctga gctggtgggt gaatggcaag    540
gaggtccaca gtggggtcag cacgaccct caggcctaca aggagagcaa ttatagctac    600
tgcctgagca gccgcctgag ggtctctgct accttctggc acaatcctcg aaaccacttc    660
cgctgccaag tgcagttcca tgggctttca gaggaggaca gtggccaga gggctcaccc    720 aaacctgtca cacagaacat cagtgcagag gcctggggcc gagcagactg tggaatcact    780
tcagcatcct atcatcaggg ggttctgtct gcaaccatcc tctatgagat cctactgggg    840
aaggccaccc tatatgctgt gctggtcagt ggcctggtgc tgatggccat ggtcaagaaa    900
aaaaattcct ga                                                       912
```

<210> SEQ ID NO 21
<211> LENGTH: 408
<212> TYPE: DNA
<213> ORGANISM: Artificial Sequence
<220> FEATURE:
<223> OTHER INFORMATION: Synthetic

<400> SEQUENCE: 21

```
atgacactga aaatggactc aagccctgga ttcgtggctg tcatcctgct gattctgggc     60
cggactcacg gggatagcgt gacccagaca gagggccagg tgaccgtctc cgaatctaag    120
agtctgatca ttaactgtac ctactccgcc acatctatcg ggtatcctaa tctgttctgg    180
tacgtgcgct atccaggcga ggggctgcag ctgctgctga aagtcattac cgctgggcag    240
aagggatcct ctcgaggatt cgaggcaaca tacaacaaag aagccacttc atttcatctg    300
cagaaggcaa gcgtgcagga atcagatagc gccgtgtact attgcgcact gtggtccggc    360
tcttggcagc tgatctttgg atccggcacc cagctgacag tgatgccc               408
```

<210> SEQ ID NO 22
<211> LENGTH: 393
<212> TYPE: DNA
<213> ORGANISM: Artificial Sequence
<220> FEATURE:
<223> OTHER INFORMATION: Synthetic

<400> SEQUENCE: 22

```
atggccacac gcctgctgtg ctacactgtg ctgtgcctgc tgggggctcg catcctgaac     60
tcaaaagtca tccagacacc tcgctacctg gtcaaaggcc aggggcagaa agccaagatg    120
agatgcatcc ctgagaaggg gcacccagtg gtcttctggt accagcagaa caaaaacaat    180
gagttcaagt ttctgatcaa ctttcagaat caggaagtgc tgcagcagat tgatatgacc    240
gagaagcggt tctcagccga atgcccaagc aattcccct gtagcctgga tccagagc     300 tccgaagccg cgatagcgc cctgtacctg tgcgctagca gagactcccc agagcagtat    360
tttggacccg gcacaagact gactgtgctg gaa                                 393
```

<210> SEQ ID NO 23
<211> LENGTH: 9
<212> TYPE: PRT
<213> ORGANISM: Artificial Sequence
<220> FEATURE:
<223> OTHER INFORMATION: Synthetic

<400> SEQUENCE: 23

Ser Leu Ala Met Trp Ile Thr Gln Cys
1               5

```
<210> SEQ ID NO 24
<211> LENGTH: 9
<212> TYPE: PRT
<213> ORGANISM: Artificial Sequence
<220> FEATURE:
<223> OTHER INFORMATION: Synthetic

<400> SEQUENCE: 24

Ser Leu Leu Ala Trp Ile Thr Gln Cys
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic

<400> SEQUENCE: 25

Ser Leu Leu Met Ala Ile Thr Gln Cys
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic

<400> SEQUENCE: 26

Ser Leu Leu Met Trp Ala Thr Gln Cys
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic

<400> SEQUENCE: 27

Ser Leu Leu Met Trp Ile Ala Gln Cys
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic

<400> SEQUENCE: 28

Ser Leu Leu Met Trp Ile Thr Ala Cys
1               5
```